United States Patent
Abe et al.

(10) Patent No.: US 9,040,314 B2
(45) Date of Patent: May 26, 2015

(54) RESIN COATING DEVICE, AND RESIN COATING METHOD

(75) Inventors: Seikou Abe, Osaka (JP); Masaru Nonomura, Osaka (JP); Kei Tsunemasa, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/232,716

(22) PCT Filed: Sep. 11, 2012

(86) PCT No.: PCT/JP2012/005757
§ 371 (c)(1),
(2), (4) Date: Jan. 14, 2014

(87) PCT Pub. No.: WO2013/121473
PCT Pub. Date: Aug. 22, 2013

(65) Prior Publication Data
US 2014/0199790 A1    Jul. 17, 2014

(30) Foreign Application Priority Data

Feb. 16, 2012    (JP) ................................. 2012-031285

(51) Int. Cl.
*H01L 21/66* (2006.01)
*H01L 23/00* (2006.01)
*G01N 21/64* (2006.01)

(52) U.S. Cl.
CPC ......... *H01L 22/24* (2013.01); *H01L 2933/0041* (2013.01); *H01L 24/97* (2013.01); *H01L 2224/48091* (2013.01); *H01L 2224/49107* (2013.01); *H01L 2224/73265* (2013.01);

(Continued)

(58) Field of Classification Search
USPC ............................................... 438/7; 118/697
See application file for complete search history.

(56) References Cited

U.S. PATENT DOCUMENTS

2001/0020519 A1*  9/2001  Oh ................................ 156/500
2006/0029724 A1   2/2006  Babiarz et al.
(Continued)

FOREIGN PATENT DOCUMENTS

JP    2011-096936 A    5/2001
JP    2003-260403 A    9/2003
(Continued)

OTHER PUBLICATIONS

International Search Report for Application No. PCT/JP2012/005757 dated Nov. 27, 2012.

Primary Examiner — Charles Garber
Assistant Examiner — Stanetta Isaac
(74) Attorney, Agent, or Firm — Pearne & Gordon LLP

(57) ABSTRACT

A translucent member 41 that has been trial-coated with a resin 8 for measurement of a light emission characteristic is placed on a translucent member placement portion 53, an excitation light that excites a phosphor is emitted from a light source unit 42 disposed above, the resin 8 coated on the translucent member 41 is irradiated with the excitation light from above, a deviation between a measurement result obtained by measuring the light emission characteristic of the light emitted from the resin 8, and a light emission characteristic specified in advance is obtained, and an appropriate resin coating amount of the resin to be coated on the LED element for actual production is derived on the basis of the deviation.

5 Claims, 29 Drawing Sheets

(52) U.S. Cl.
CPC .................. *H01L2924/3025* (2013.01); *H01L 2224/92247* (2013.01); *G01N 21/645* (2013.01); *H01L 2924/12041* (2013.01)

(56) References Cited

U.S. PATENT DOCUMENTS

| | | |
|---|---|---|
| 2007/0001180 A1 | 1/2007 | Obara et al. |
| 2008/0137106 A1 | 6/2008 | Ono |
| 2008/0206802 A1 | 8/2008 | Taninaka et al. |
| 2010/0129525 A1 | 5/2010 | Shida et al. |
| 2011/0184569 A1* | 7/2011 | Abernathy et al. ........... 700/283 |

FOREIGN PATENT DOCUMENTS

| | | |
|---|---|---|
| JP | 2006-093108 A | 4/2006 |
| JP | 2007-066969 A | 3/2007 |
| JP | 2007-289081 A | 11/2007 |
| JP | 2008-145300 A | 6/2008 |
| WO | 2006/121197 A1 | 11/2006 |
| WO | 2012/056604 A1 | 5/2012 |
| WO | 2012/056605 A1 | 5/2012 |

* cited by examiner

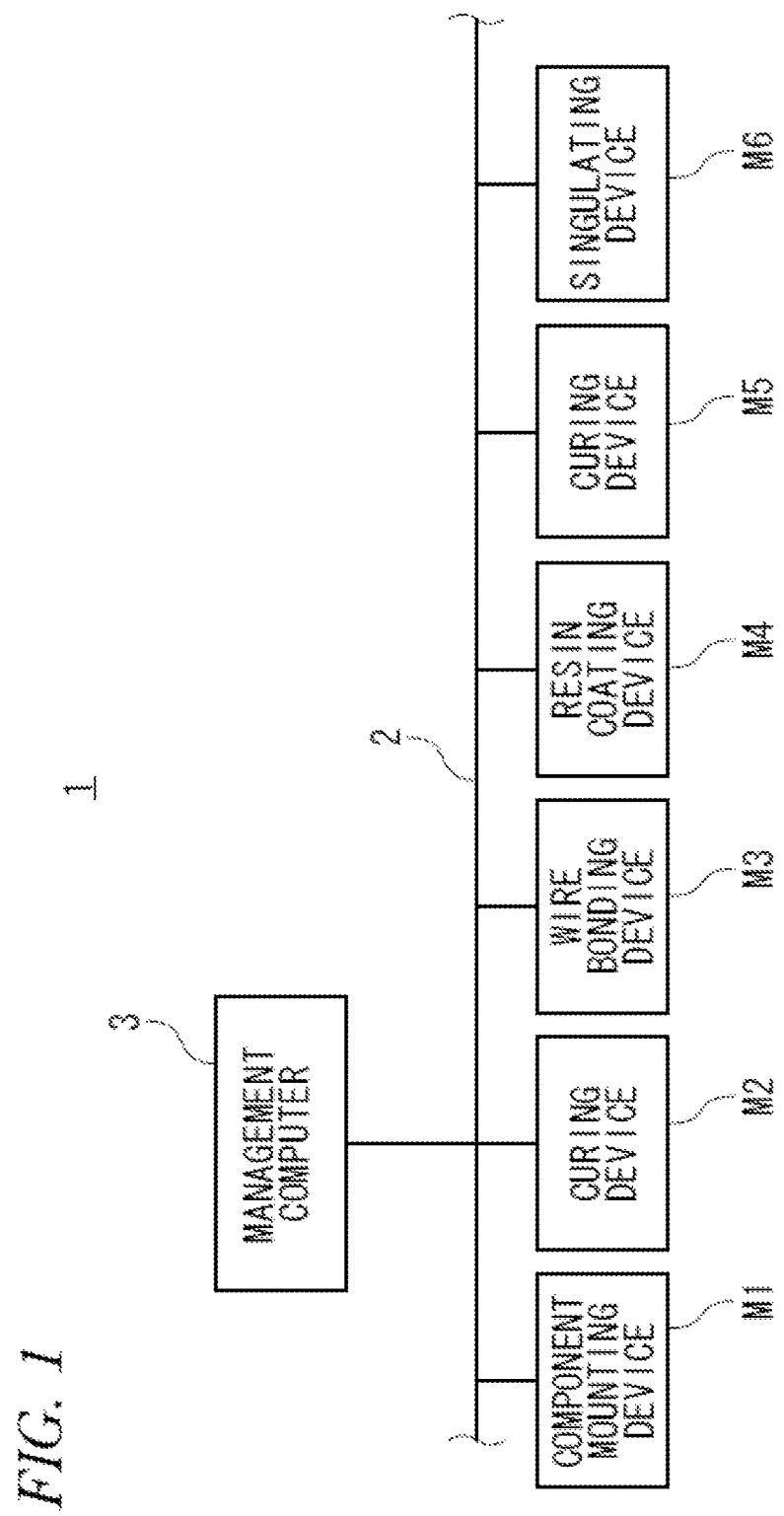

FIG. 3A
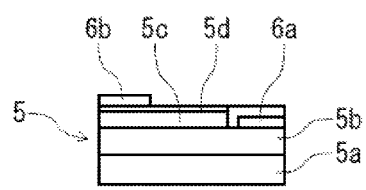
FIG. 3B
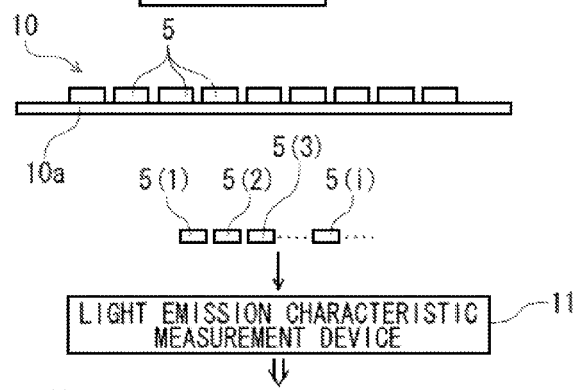
FIG. 3C
FIG. 3D
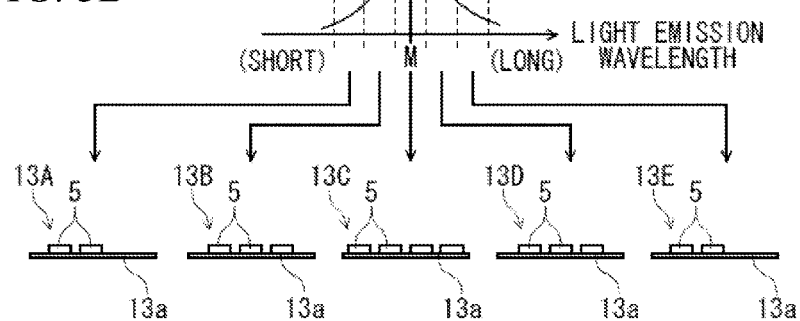

FIG. 4

| PHOSPHOR CONCENTRATION (%) | Bin CODE CLASSIFICATION-SPECIFIC APPROPRIATE RESIN COATING AMOUNT SHORT<<<(WAVELENGTH 465 nm)>>>LONG | | | | |
|---|---|---|---|---|---|
| | [1] | [2] | [3] | [4] | [5] |
| D1 (5%) | VA0 | VB0 | VC0 | VD0 | VE0 |
| D2 (10%) | VF0 | VG0 | VH0 | VJ0 | VK0 |
| D3 (15%) | VL0 | VM0 | VN0 | VP0 | VR0 |

FIG. 24A

| | | SHORT <<< (WAVELENGTH 465nm) >>> LONG | | | | |
|---|---|---|---|---|---|---|
| 12b | BIN CODE | [1] | [2] | [3] | [4] | [5] |
| 15(1) | APPROPRIATE RESIN COATING AMOUNT PURE 5% RESIN | VA0 | VB0 | VC0 | VD0 | VE0 |
| 39a(1) | LIGHT EMISSION CHARACTERISTIC MEASUREMENT VALUE CHROMATICITY COORDINATES Z | ZA0 $(X_{A0}, Y_{A0})$ | ZB0 $(X_{B0}, Y_{B0})$ | ZC0 $(X_{C0}, Y_{C0})$ | ZD0 $(X_{D0}, Y_{D0})$ | ZE0 $(X_{E0}, Y_{E0})$ |
| 81a(1) | THRESHOLD VALUE | ZA0 ±10% | ZB0 ±10% | ZC0 ±10% | ZD0 ±10% | ZE0 ±10% |

FIG. 24B

| | | SHORT <<< (WAVELENGTH 465nm) >>> LONG | | | | |
|---|---|---|---|---|---|---|
| 12b | BIN CODE | [1] | [2] | [3] | [4] | [5] |
| 15(2) | APPROPRIATE RESIN COATING AMOUNT PURE 10% RESIN | VF0 | VG0 | VH0 | VJ0 | VK0 |
| 39a(2) | LIGHT EMISSION CHARACTERISTIC MEASUREMENT VALUE CHROMATICITY COORDINATES Z | ZF0 $(X_{F0}, Y_{F0})$ | ZG0 $(X_{G0}, Y_{G0})$ | ZH0 $(X_{H0}, Y_{H0})$ | ZJ0 $(X_{J0}, Y_{J0})$ | ZK0 $(X_{K0}, Y_{K0})$ |
| 81a(2) | THRESHOLD VALUE | ZF0 ±10% | ZG0 ±10% | ZH0 ±10% | ZJ0 ±10% | ZK0 ±10% |

FIG. 24C

| | | SHORT <<< (WAVELENGTH 465nm) >>> LONG | | | | |
|---|---|---|---|---|---|---|
| 12b | BIN CODE | [1] | [2] | [3] | [4] | [5] |
| 15(3) | APPROPRIATE RESIN COATING AMOUNT PURE 15% RESIN | VL0 | VM0 | VN0 | VP0 | VR0 |
| 39a(3) | LIGHT EMISSION CHARACTERISTIC MEASUREMENT VALUE CHROMATICITY COORDINATES Z | ZL0 $(X_{L0}, Y_{L0})$ | ZM0 $(X_{M0}, Y_{M0})$ | ZN0 $(X_{N0}, Y_{N0})$ | ZP0 $(X_{P0}, Y_{P0})$ | ZR0 $(X_{R0}, Y_{R0})$ |
| 81a(3) | THRESHOLD VALUE | ZL0 ±10% | ZM0 ±10% | ZN0 ±10% | ZP0 ±10% | ZR0 ±10% |

*FIG. 27A*
TRIAL COATING

|  | SHORT <<< (WAVELENGTH 465nm) >>> LONG | | | | |
|---|---|---|---|---|---|
| BIN CODE | [1] | [2] | [3] | [4] | [5] |
| ACTUAL RESIN COATING AMOUNT | VA1 | VB1 | VC1 | VD1 | VE1 |

*FIG. 27B*
LIGHT EMISSION CHARACTERISTIC MEASUREMENT

| LIGHT EMISSION CHARACTERISTIC MEASUREMENT VALUE CHROMATICITY COORDINATES Z | ZA1 $(X_{A1}, Y_{A1})$ | ZB1 $(X_{B1}, Y_{B1})$ | ZC1 $(X_{C1}, Y_{C1})$ | ZD1 $(X_{D1}, Y_{D1})$ | ZE1 $(X_{E1}, Y_{E1})$ |
|---|---|---|---|---|---|
| DEVIATION | $\Delta X_A\ \Delta Y_A$ | $\Delta X_B\ \Delta Y_B$ | $\Delta X_C\ \Delta Y_C$ | $\Delta X_D\ \Delta Y_D$ | $\Delta X_E\ \Delta Y_E$ |

*FIG. 27C*
COMPARISON BETWEEN DEVIATION AND THRESHOLD VALUE

| DEVIATION | $\Delta X_A\ \Delta Y_A$ | $\Delta X_B\ \Delta Y_B$ | $\Delta X_C\ \Delta Y_C$ | $\Delta X_D\ \Delta Y_D$ | $\Delta X_E\ \Delta Y_E$ |
|---|---|---|---|---|---|
| THRESHOLD VALUE | ZA0 ±10% | ZB0 ±10% | ZC0 ±10% | ZD0 ±10% | ZE0 ±10% |

DEVIATION ≦ THRESHOLD VALUE
   EXECUTE PRODUCTION COATING OPERATION WITH PRESET APPROPRIATE RESIN COATING AMOUNTS VA0, VB0, VC0, VD0, AND VE0

DEVIATION > THRESHOLD VALUE

*FIG. 27D*
DERIVE NEW APPROPRIATE RESIN COATING AMOUNT

|  | SHORT <<< (WAVELENGTH 465nm) >>> LONG | | | | |
|---|---|---|---|---|---|
| BIN CODE | [1] | [2] | [3] | [4] | [5] |
| CORRECTED APPROPRIATE RESIN COATING AMOUNT | VA2 | VB2 | VC2 | VD2 | VE2 |

\* VA2, VB2, VC2, VD2, AND VE2 ARE UPDATED VALUES OBTAINED BY ADDING CORRECTIONS CORRESPONDING TO RESPECTIVE DEVIATIONS TO VA0, VB0, VC0, VD0, AND VE0

RESIN COATING DEVICE, AND RESIN COATING METHOD

TECHNICAL FIELD

The present invention relates to a resin coating device and a resin coating method which are used in an LED package manufacturing system for manufacturing an LED package in which an LED element mounted on a substrate is covered with a resin containing a luminescent material therein.

BACKGROUND ART

In recent years, as light sources for a variety of illuminating devices, LEDs (light emitting diodes) having such excellent characteristics that a power consumption is low, and a lifetime is long have been extensively used. Fundamental lights emitted by an LED element are limited to three lights of red, green, and blue as of now, and therefore in order to obtain a preferable white light for a general illumination purpose, there is used a method for obtaining the white light by additively mixing the above-mentioned three fundamental lights together, or a method for obtaining a false white color by combination of a blue LED with a phosphor that emits a fluorescence of yellow having a complementary relationship with blue. In recent years, the latter has been more extensively used, and the illuminating device using an LED package in which the blue LED and a YAG phosphor are combined together has been used for a backlight of a liquid crystal panel (for example, refer to Patent Literature 1).

In this Patent Literature example, after an LED element has been mounted on a bottom surface of a recessed mounting portion having a side wall formed with a reflection surface, a silicon resin or an epoxy resin into which YAG phosphor grains are dispersed is poured into the mounting portion into which the YAG phosphor grains are dispersed to form a resin package portion, to thereby configure the LED package. The Patent Literature example also discloses an example in which for the purpose of equalizing a height of the resin package portion within the mounting portion into which the resin has been poured, an excessive resin storage portion is formed for discharging and storing an excessive resin poured by a specified amount or more from the mounting portion. With this configuration, even if the amount of discharge from a dispenser is varied at the time of pouring the resin, the resin package portion having a given amount of resin with a specified height is formed on the LED element.

CITATION LIST

Patent Literature

Patent Literature 1: JP-A-2007-66969

SUMMARY OF INVENTION

Technical Problem

However, in the above-mentioned prior art example, there arises such a problem that a variation in a light emission wavelength of the individual LED elements causes a variation in the light emission characteristic of the LED packet as a product. That is, the LED element is subjected to a manufacturing process for forming a plurality of elements on a wafer in a lump, and a variety of error factors in the manufacturing process, for example, the unevenness of a composition at the time of forming a film on the wafer is not prevented from causing a variation in the light emission wavelength of the LED elements singulated from a wafer state. In the above-mentioned example, since the height of the resin package portion that covers the LED element is equalized, the variation in the light emission wavelength of the singulated LED elements is reflected on the variation in the light emission characteristic of the LED package as a product as it is, which results in defectives falling outside a quality permissible range being obliged to increase. In this way, the conventional LED package manufacturing technique suffers from such a problem that the variation in the light emission wavelength of the singulated LED elements causes the variation in the light emission characteristic of the LED package as the product, thereby leading to a reduction in a production yield.

Under the above circumstances, an object of the present invention is to provide a resin coating device and a resin coating method, which can equalize the light emission characteristic of the LED package to improve the production yield even if the light emission wavelengths of the simulated LED elements are varied in the LED package manufacturing system.

Solution to Problem

According to one aspect of the present invention, there is provided a resin coating device that coats a resin over an LED element mounted on a substrate for use in an LED package manufacturing system that manufactures an LED package in which the LED element mounted on the substrate is covered with the resin containing a phosphor therein, the resin coating device comprising:

a resin coating unit that discharges the resin with a variable coating amount to coat the resin at an arbitrary position to be coated;

a coating control unit that executes measurement coating processing for trial-coating a translucent member reeled off by a recovery reel while being reeled out of a supply reel with a resin for measurement of a light emission characteristic while controlling the resin coating unit, and production coating processing for coating the resin on the LED element for actual production;

a light source unit that emits an excitation light that excites the phosphor;

a translucent member placement portion on which the translucent member that has been trial-coated with the resin in the measurement coating processing is placed;

a light emission characteristic measurement unit that measures the light emission characteristic of a light emitted from the resin by irradiating the resin coated on the translucent member with the excitation light emitted from the light source unit;

a coating amount derivation processing unit that derives an appropriate resin coating amount of the resin to be coated on the LED element for the actual production on the basis of a measurement result of the light emission characteristic measurement unit and a light emission characteristic specified in advance; and a production execution processing unit that instructs the coating control unit about the appropriate resin coating amount to execute the production coating processing for coating the appropriate resin coating amount of resin on the LED element.

According to another aspect of the present invention, there is provided a resin coating method according to one aspect of the present invention that coats a resin over an LED element mounted on a substrate for use in an LED package manufacturing system that manufactures an LED package in which the LED element mounted on the substrate is covered with the resin containing a phosphor therein, the resin coating method comprising:

a measurement coating step of trial-coating a translucent member reeled off by a recovery reel while being reeled out of a supply reel with a resin for measurement of a light emission characteristic;

a translucent member placing step of placing the translucent member trial-coated with the resin on a translucent member placement portion;

a light emission characteristic measuring step of measuring the light emission characteristic of a light emitted from the resin by irradiating the resin coated on the translucent member with an excitation light emitted from a light source unit that emits the excitation light for exciting the phosphor;

a coating amount derivation processing step of deriving an appropriate resin coating amount of the resin to be coated on the LED element for the actual production on the basis of a measurement result in the light emission characteristic measurement step, and a light emission characteristic specified in advance; and a production executing step of instructing a coating control unit that controls the resin discharge unit about the derived appropriate resin coating amount, to execute the production coating processing for coating the appropriate resin coating amount of resin on the LED element.

Advantageous Effects of Invention

According to the present invention, in resin coating used in manufacture of the LED package in which the LED element is covered with the resin containing the phosphor therein, the translucent member trial-coated with the resin for measurement of the light emission characteristic is placed on the translucent member placement portion, an excitation light that excites the phosphor is emitted from the light source unit arranged above, the resin coated on the translucent member is irradiated with the excitation light from above, the deviation between the measurement result obtained by measuring the light emission characteristic of the light emitted from the resin, and a light emission characteristic specified in advance is obtained, and an appropriate resin coating amount of the resin to be coated on the LED element for actual production is derived on the basis of the deviation. As a result, even if the light emission wavelengths of the singulated LED elements are varied, the light emission characteristics of the LED packages can be equalized to improve the production yield. Also, since the translucent member is reeled off by the recovery reel while being reeled out of the supply reel, not only a disposal of the used translucent member can be facilitated, but also the forward movement and the backward movement of the translucent member can be smoothed with the rotation of the recovery reel together with the supply reel. Also, since the supply reel and the recovery reel are disposed on the same shaft member, the overall resin coating device can be downsized.

BRIEF DESCRIPTION OF DRAWINGS

[FIG. 1] FIG. 1 is a block diagram illustrating a configuration of an LED package manufacturing system according to an embodiment of the present invention.

[FIG. 2]

[FIG. 3] FIGS. 3A to 3D are illustrative views of a supply configuration and element characteristic information of an LED element used in the LED package manufacturing system according to the embodiment of the present invention.

[FIG. 4] FIG. 4 is an illustrative view of resin coating information used in the LED package manufacturing system according to the embodiment of the present invention.

[FIG. 5]

FIG. 6 is an illustrative view of map data used in the LED package manufacturing system according to the embodiment of the present invention.

[FIG.7]

FIG. 8 is an illustrative view of a light emission characteristic inspection function provided in the resin coating device in the LED package manufacturing system according to the embodiment of the present invention.

FIG. 9 is a diagram illustrating a state in which a resin is discharged onto an emboss tape by the LED package manufacturing system according to the embodiment of the present invention.

FIG. 10 is an illustrative view of a light emission characteristic inspection function provided in the resin coating device in the LED package manufacturing system according to the embodiment of the present invention.

FIG. 11 is a partially cross-sectional side view of a part of a trial coating/measurement unit provided in the LED package manufacturing system according to the embodiment of the present invention.

FIG. 12 is a partially cross-sectional exploded side view of a part of the trial coating/measurement unit provided in the LED package manufacturing system according to the embodiment of the present invention.

[FIG. 13]

[FIG. 14]

[FIG. 15]

[FIG. 16]

[FIG. 17]

[FIG. 18]

[FIG. 19]

[FIG. 20]

FIG. 21 is a block diagram illustrating a configuration of a control system in the LED package manufacturing system according to the embodiment of the present invention.

FIG. 22 is a flowchart of LED package manufacture by the LED package manufacturing system according to the embodiment of the present invention.

FIG. 23 is a flowchart of a threshold value data creation processing for determination of non-defective products in the LED package manufacturing system according to the embodiment of the present invention.

[FIG. 24] FIGS. 24A to 24C are illustrative views of threshold value data for determination of the non-defective products in the LED package manufacturing system according to the embodiment of the present invention.

FIG. 25 is a chromaticity diagram illustrating the threshold value data for determination of the non-defective products in the LED package manufacturing system according to the embodiment of the present invention.

FIG. 26 is a chromaticity diagram illustrating resin coating work processing in an LED package manufacturing process by the LED package manufacturing system according to the embodiment of the present invention.

[FIG. 27] FIGS. 27A to 27D are illustrative views of the resin coating work processing in the LED package manufacturing process by the LED package manufacturing system according to the embodiment of the present invention.

[FIG. 28]

[FIG. 29]

DESCRIPTION OF EMBODIMENTS

Figure 2A:
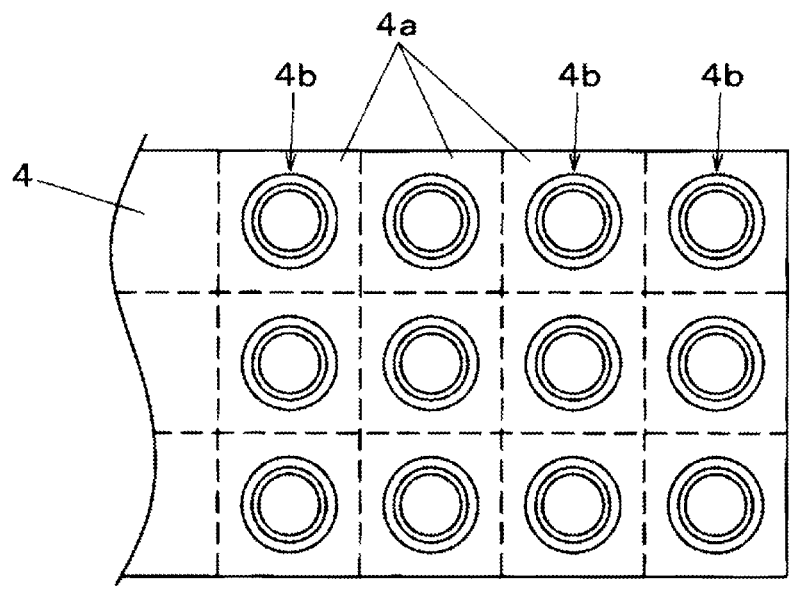
FIGS. 2A and 2B are illustrative views of a configuration of an LED package manufactured by the LED package manufacturing system according to the embodiment of the present invention.

Subsequently, embodiments of the present invention will be described with reference to the drawings. First, a configuration of an LED package manufacturing system 1 will be described with reference to FIG. 1. The LED package manufacturing system 1 has a function of manufacturing an LED package in which an LED element mounted on a substrate is covered with a resin containing a phosphor therein. In this embodiment, as illustrated in FIG. 1, the respective devices of a component mounting device M1, a curing device M2, a wire bonding device M3, a resin coating device M4, a curing device M5, and a singulating device M6 are connected to each other by an LAN system 2, and those respective devices are overall controlled by a management computer 3.

The component mounting device M1 bonds an LED element 5 onto a substrate 4 (refer to FIGS. 2A and 2B) which is a base of the LED package with a resin adhesive for mounting. The curing device M2 heats the substrate 4 on which the LED element 5 has been mounted, to thereby cure the resin adhesive used for bonding in the mounting operation. The wire bonding device M3 connects electrodes of the substrate 4 to electrodes of the substrate 4 by bonding wires. The resin coating device M4 coats a resin containing a phosphor therein on each LED element 5 on the substrate 4 that has been subjected to the wire bonding. The curing device M5 heats the substrate 4 on which has been coated with the resin, to thereby cure the resin coated over the LED element 5. The singulating device M6 cuts the substrate 4 after the resin has been cured for each of the individual LED elements 5, and singulates the substrate 4 into the respective LED packages. With this processing, the singulated LED package is completed.

FIG. 1 illustrates an example in which the respective devices of the component mounting device M1 to the singulating device M6 are arranged in series to configure a production line. However, the LED package manufacturing system 1 does not always employ this line configuration, but the operation in the respective steps may be sequentially executed by the respectively dispersed devices so far as an information transmission to be described below is appropriately conducted. Also, a plasma processing device that conducts plasma processing for the purpose of cleaning the electrodes prior to the wire bonding, and a plasma processing device that conducts the plasma processing for the purpose of reforming the surface to improve the adhesion of the resin prior to the resin coating after the wire bonding may intervened before and after the wire bonding device M3.

Now, a description will be given of the substrate 4, the LED element 5, and an LED package PKG as a completed product, which are to be operated in the LED package manufacturing system 1, with reference to FIGS. 2A, 2B, and 3A to 3D. As illustrated in FIG. 2A, the substrate 4 is a multiple substrate in which a plurality of singulated substrates 4a each configuring a base of one LED package PKG in the completed product are produced. One LED mounting portion 4b on which each LED element 5 is mounted is formed on each of the singulated substrates 4a. The LED element 5 is mounted within the LED mounting portion 4b for each of the singulated substrates 4a, and thereafter a resin 8 is coated over the LED element 5 within the LED mounting portion 4b. Further, the substrate 4 that has been processed is singulated for each of the singulated substrates 4a after the resin 8 has been cured, to thereby complete the LED package PKG illustrated in FIG. 2B.

Figure 2B:
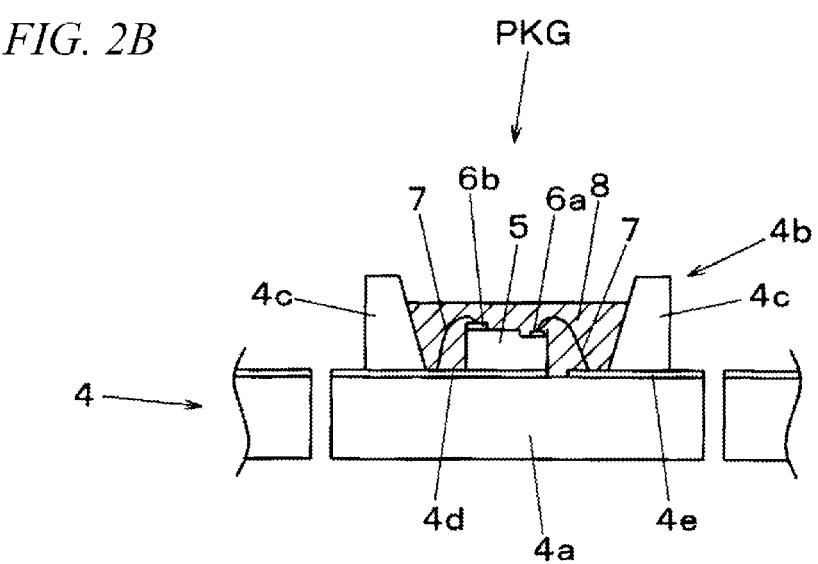

The LED package PKG has a function of applying a white light used as a light source of a variety of illuminating devices, and combines the LED element 5 which is a blue LED with the resin 8 containing the phosphor that emits a fluorescence of yellow having a complementary relationship with blue, to thereby obtain a false white light. As illustrated in FIG. 2B, a cavity-shaped reflection portion 4c having, for example, a circular or oval annular dam forming the LED mounting portion 4b is disposed on the singulated substrate 4a. An n-type portion electrode 6a and a p-type portion electrode 6b of the LED element 5 mounted inside of the reflection portion 4c are connected to wiring layers 4e and 4d formed on an upper surface of the singulated substrate 4a by bonding wires 7, respectively. The resin 8 is coated over the LED element 5 of this state inside the reflection portion 4c with a given thickness, and in a process in which the blue light emitted from the LED element 5 penetrates through the resin 8, and is applied, the blue light is mixed with yellow emitted by the phosphor contained within the resin 8, and applied as the white light.

As illustrated in FIG. 3A, the LED element 5 is configured so that an n-type semiconductor 5b and a p-type semiconductor 5c are laminated on a sapphire substrate 5a, and a surface of the p-type semiconductor 5c is covered with a transparent electrode 5d. The n-type portion electrode 6a and the p-type portion electrode 6b for external connection are formed on the n-type semiconductor 5b and the p-type semiconductor 5c, respectively. As illustrated in FIG. 3B, after a plurality of LED elements 5 have been formed in a lump, the LED elements 5 are singulated, and extracted from an LED wafer 10 adhesively retained on a retention sheet 10a. A variety of error factors in the manufacturing process, for example, the unevenness of a composition at the time of forming the film on the wafer is not prevented from causing a variation in the light emission wavelength such as the light emission wavelength of the LED elements 5 singulated from a wafer state. When such LED elements 5 are mounted on the respective substrate 4 as they are, the light emission characteristics of the LED packages PKG are varied as the products.

In order to prevent defects in quality caused by the variation of the light emission characteristic, in this embodiment, the light emission characteristics of the plurality of LED elements 5 manufactured in the same manufacturing step are measured in advance, element characteristic information associating the respective LED elements 5 with the light emission characteristics of the LED elements 5 is created in advance, and an appropriate amount of resin 8 corresponding to the light emission characteristics of the respective LED elements 5 is coated in the coating of the resin 8. Then, in order to coat the appropriate amount of resin 8, resin coating information to be described later is prepared in advance.

First, the element characteristic information will be described. As illustrated in FIG. 3C, element IDs (in this example, the individual LED elements 5 are identified by serial No. (i) in the LED wafer 10) for identifying the respective LED elements 5 are allocated to the LED elements 5 extracted from the LED wafer 10, and the LED elements 5 are then sequentially supplied to a light emission characteristic measurement device 11. If the element IDs are information that can specify the LED elements 5, individually, other data formats, for example, matrix coordinates indicative of an array of the LED elements 5 in the LED wafer 10 may be used as they are. With the use of the element IDs of this format, the LED element 5 can be supplied in the state of the LED wafer 10 in the component mounting device M1 which will be described later.

In the light emission characteristic measurement device 11, an electric power is supplied to the respective LED elements 5 through probes to actually emit a light, and the light is subjected to spectrometry to measure given items such as the light emission wavelength and a light emission intensity. In the LED elements 5 to be measured, a standard distribution of the light emission wavelength is prepared as reference data in advance, and a wavelength range corresponding to a standard range in the distribution is sectioned into a plurality of wavelength bands, to thereby rank the plurality of LED elements 5 to be measured according to the light emission wavelength. In this example, Bin codes [1], [2], [3], [4], and [5] are allocated to the respective ranks set by sectioning the wavelength range into five sub-ranges in order from a low wavelength side. Then, the element characteristic information 12 that associates element ID 12a with Bin code 12b is created.

That is, the element characteristic information 12 is information obtained by measuring the light emission characteristics containing the light emission wavelengths of the plurality of LED elements 5, individually, in advance. The element characteristic information 12 is prepared by LED element manufacturers, or the like, in advance, and transmitted to the LED package manufacturing systems 1. As a transmission mode of the element characteristic information 12, the element characteristic information 12 may be recorded in a single storage medium for transmission. Also, the element characteristic information 12 may be transmitted to the management computer 3 through the LAN system 2. In any cases, the transmitted element characteristic information 12 is stored in the management computer 3, and supplied to the component mounting device M1 as occasion demands.

In this way, the plurality of LED elements 5 that have been subjected to the light emission characteristic measurement are sorted for each of the characteristic ranks as illustrated in FIG. 3D, sorted into five types according to the respective characteristic ranks, and stuck onto five adhesive sheets 13a, individually. As a result, three kinds of LED sheets 13A, 13B, 13C, 13D, and 13E in which the LED elements 5 corresponding to the respective Bin codes [1], [2], [3], [4], and [5] are adhesively retained onto the adhesive sheets 13a are created. When the respective LED elements 5 are mounted on the singulated substrates 4a of the substrate 4, the LED elements 5 are supplied to the component mounting device M1 in the configurations of the LED sheets 13A, 13B, 13C, 13D, and 13E that have already been ranked in this way. In this situation, the element characteristic information 12 indicating that the LED element 5 corresponding to any one of the Bin codes [1], [2], [3], [4], and [5] is retained onto each of the LED sheets 13A, 13B, 13C, 13D, and 13E is provided from the management computer 3.

Subsequently, the resin coating information prepared in correspondence with the above-mentioned element characteristic information 12 in advance will be described with reference to FIG. 4. In the LED package PKG configured to combine the blue LED with the phosphor of a YAG system to obtain the white light, the blue light emitted by the LED element 5, and the yellow light emitted from the phosphor excited by the blue light are additively mixed together. Therefore, the amount of phosphor grains within the recessed LED mounting portion 4b in which the LED element 5 is mounted is important in ensuring a regular light emission characteristic of the LED package PKG of the product.

As described above, since a variation classified by the Bin codes [1], [2], [3], [4], and [5] is present in the light emission wavelength of the plurality of LED elements 5 to be operated at the same time, an appropriate amount of phosphor grains in the resin 8 coated over the LED element 5 is different according to the Bin codes [1], [2], [3], [4], and [5]. In resin coating information 14 prepared in this embodiment, as illustrated in FIG. 4, a Bin classification-specific appropriate resin coating amount is specified according to a Bin code classification 17 by the nl (nanoliter) in advance. That is, when the resin 8 is precisely coated over the LED element 5 by the appropriate resin coating amount indicated by the resin coating information 14, the amount of phosphor grains in the resin that covers the LED element 5 becomes an appropriate amount of phosphor grains. As a result, a regular light emission wavelength required for the completed product after the resin has been thermally cured is ensured.

In this example, the phosphor concentrations indicative of the concentrations of the phosphor grains in the resin 8 are set to plural values (in this example, D1 (5%), D2 (10%), D3 (15%)), and an appropriate (uncomfortable feeling in expression) numerical value is also used for the appropriate resin coating amount of resin 8 according to the phosphor concentration of the resin 8 to be used. That is, when the resin of the phosphor concentration D1 is coated, the resin 8 of appropriate resin coating amounts VA0, VB0, VC0, VD0, and VE0 (appropriate resin coating amount 15(1)) is coated in the Bin codes [1], [2], [3], [4], and [5], respectively. Likewise, when the resin of the phosphor concentration D2 is coated, the resin 8 of appropriate resin coating amounts VF0, VG0, VH0, VJ0, and VK0 (appropriate resin coating amount 15(2)) is coated in the Bin codes [1], [2], [3], [4], and [5], respectively. Also, when the resin of the phosphor concentration D3 is coated, the resin 8 of appropriate resin coating amounts VL0, VM0, VN0, VP0, and VR0 (appropriate resin coating amount 15(3)) is coated in the Bin codes [1], [2], [3], [4], and [5], respectively. The reason that the respective appropriate resin coating amounts are set for the plurality of different phosphor concentrations is because it is more preferable to coat the resin 8 of the appropriate phosphor concentration according to the degree of variation of the light emission wavelength from the viewpoint of ensuring the quality.

Figure 5A:
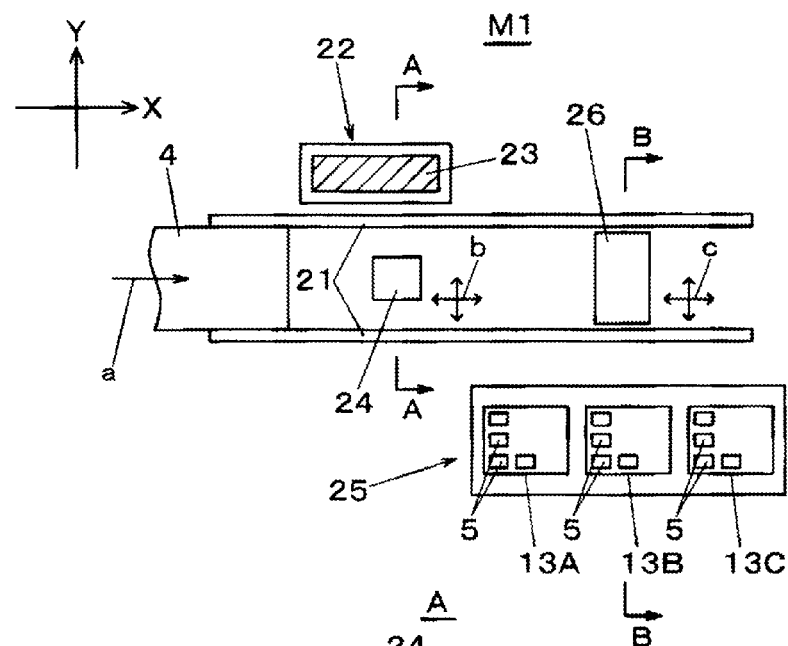
FIGS. 5A to 5C are illustrative views of a configuration and a function of a component mounting device in the LED package manufacturing system according to the embodiment of the present invention.

Subsequently, the configuration and the function of the component mounting device M1 will be described with reference to FIGS. 5A to 5C. As illustrated in a plan view of FIG. 5A, the component mounting device M1 includes a substrate transport mechanism 21 that transports the substrate 4 to be operated which has been supplied from an upstream side in a substrate transport direction (arrow a). In the substrate transport mechanism 21, an adhesive coating portion A illustrated by a cross-section A-A in FIG. 5B, and a component mounting portion B illustrated by a cross-section B-B in FIG. 4C are arranged in order from the upstream side. The adhesive coating portion A includes an adhesive supply unit 22 that is arranged on a side of the substrate transport mechanism 21, and supplies a resin adhesive 23 in the form of a coating film having a given thickness, and an adhesive transfer mechanism 24 that is movable in a horizontal direction above the substrate transport mechanism 21 and the adhesive supply unit 22. Also, the component mounting portion B is arranged on a side of the substrate transport mechanism 21, and includes a component supply mechanism 25 that holds the LED sheets 13A, 13B, 13C, 13D, and 13E illustrated in FIG. 3D, and a component mounting mechanism 26 that is movable in the horizontal direction (arrow c) above the substrate transport mechanism 21 and the component supply mechanism 25.

Figure 5B:
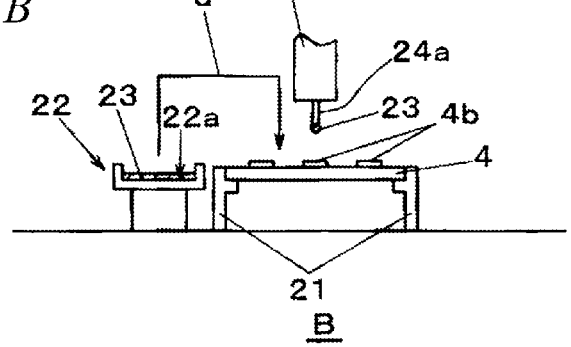

The substrate 4 carried in the substrate transport mechanism 21 is positioned in the adhesive coating portion A as illustrated in FIG. 5B, and the LED mounting portions 4b formed on the respective singulated substrates 4a are coated with the resin adhesive 23. That is, the adhesive transfer mechanism 24 is first moved to above the adhesive supply unit 22, and a transfer pin 24a is brought into contact with the coating film of the resin adhesive 23 formed on a transfer surface 22a so that the resin adhesive 23 is attached to the transfer pin 24a. Then, the adhesive transfer mechanism 24 is moved to above the substrate 4, and the transfer pin 24a is moved down to the LED mounting portion 4b (arrow d) whereby the resin adhesive 23 attached to the transfer pin 24a is supplied to an element mounting position within the LED mounting portion 4b by transfer.

Figure 5C:
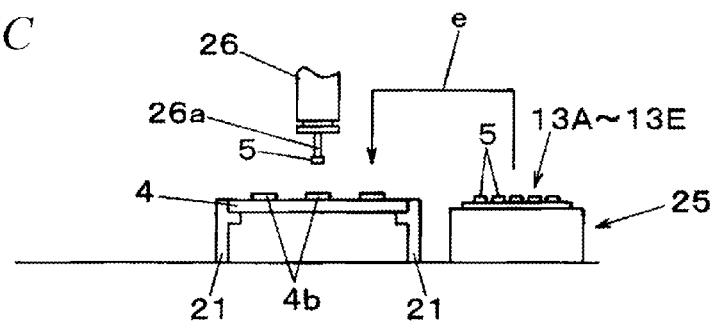

Then, the substrate 4 that has been coated with the adhesive is transported to a downstream side, and positioned in the component mounting portion B as illustrated in FIG. 5C, and the LED elements 5 are mounted on the respective LED mounting portions 4b that have been supplied with the adhesive. That is, the component mounting mechanism 26 is first moved to above the component supply mechanism 25, and a mounting nozzle 26a is moved down to any one of the LED sheets 13A, 13B, 13C, 13D, and 13E held in the component supply mechanism 25, and the LED element 5 is held and extracted by the mounting nozzle 26a. Then, the component mounting mechanism 26 is moved to above the LED mounting portion 4b of the substrate 4, and the mounting nozzle 26a is moved down (arrow e) whereby the LED element 5 held by the mounting nozzle 26a is mounted at the element mounting position coated with the adhesive within the LED mounting portion 4b.

In mounting the LED elements 5 on the substrates 4 by the component mounting device M1, an element mounting program created in advance, that is, in the individual mounting operation by the component mounting mechanism 26, the sequence of extracting the LED elements 5 from any of the LED sheets 13A, 13B, 13C, 13D, and 13E, and mounting the LED elements 5 on the plurality of singulated substrates 4a of the substrate 4 is predetermined, and the component mounting operation is executed according to the element mounting program.

Then, in the execution of the component mounting operation, mounting position information 71a (refer to FIG. 21) indicating that the individual LED elements 5 are mounted in any of the plurality of singulated substrates 4a is extracted from an operation execution history, and recorded. Then, data associating the mounting position information 71a with the element characteristic information 12 indicating that the LED elements 5 mounted the individual singulated substrates 4a correspond to any of the characteristic ranks (Bin codes [1], [2], [3], [4], and [5]) is created as map data 18 illustrated in FIG. 6 by a map creation processing unit 74 (refer to FIG. 21).

Figure 6:
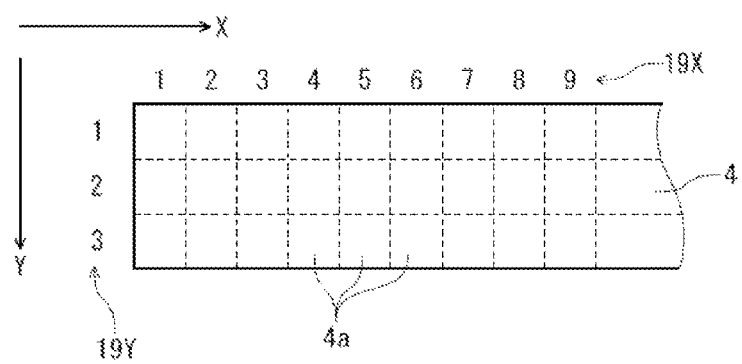
[FIG. 6]

Referring to FIG. 6, the individual positions of the plurality of singulated substrates 4a of the substrate 4 are specified by the combination of matrix coordinates 19X and 19Y indicative of respective positions in an X-direction and a Y-direction. Then, the Bin codes to which the LED elements 5 mounted at the above positions belong are made to correspond to the individual cells of a matrix configured by the matrix coordinates 19X and 19Y, to thereby create the map data 18 that associates the mounting position information 71a indicative of the positions of the LED elements 5 on the substrate 4, which have been mounted by the component mounting device M1, with the element characteristic information 12 on the LED elements 5.

That is, the component mounting device M1 includes the map creation processing unit 74 as map data creating means, which creates the map data 18 that associates the mounting position information indicative of the positions of the LED elements 5 mounted by the above device on the substrate 4 with the element characteristic information 12 on the LED elements 5, for each substrate 4. The created map data 18 is transmitted as feed forward data to the resin coating device M4 which will be described below through the LAN system 2.

Subsequently, the configuration and the function of the resin coating device M4 will be described with reference to FIGS. 7A, 7B, 17A, and 17B. The resin coating device M4 has a function of coating the resin 8 over the plurality of LED elements 5 mounted on the substrate 4 by the component mounting device M1. As illustrated in a plan view of FIG. 7A, the resin coating device M4 is configured to arrange a resin coating unit C illustrated by a cross-section C-C in FIG. 7B in a substrate transport mechanism 31 that transports the substrate 4 to be operation, which has been supplied from the upstream side, in a substrate transport direction (arrow f). A resin discharge head 32 configured to discharge the resin 8 from a discharge nozzle 33a equipped on a lower end portion thereof is disposed in the resin coating unit C.

Figure 7A:
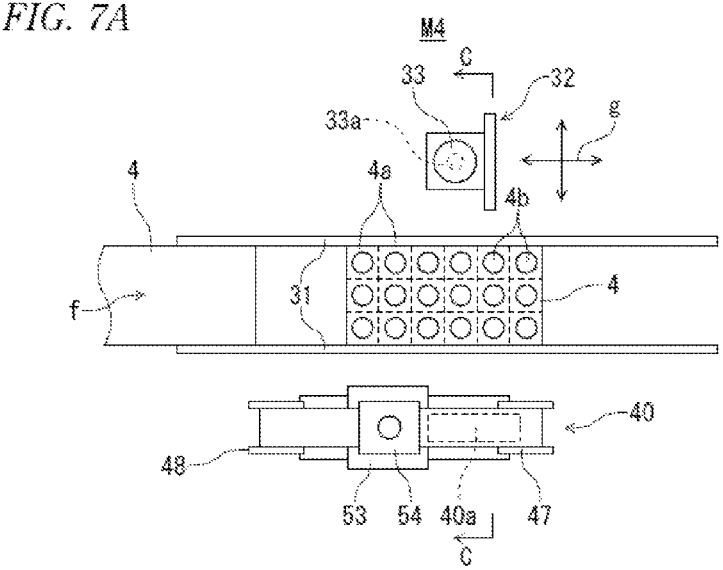
FIGS. 7A and 7B are illustrative views of a configuration and a function of a resin coating device in the LED package manufacturing system according to the embodiment of the present invention.
Figure 7B:
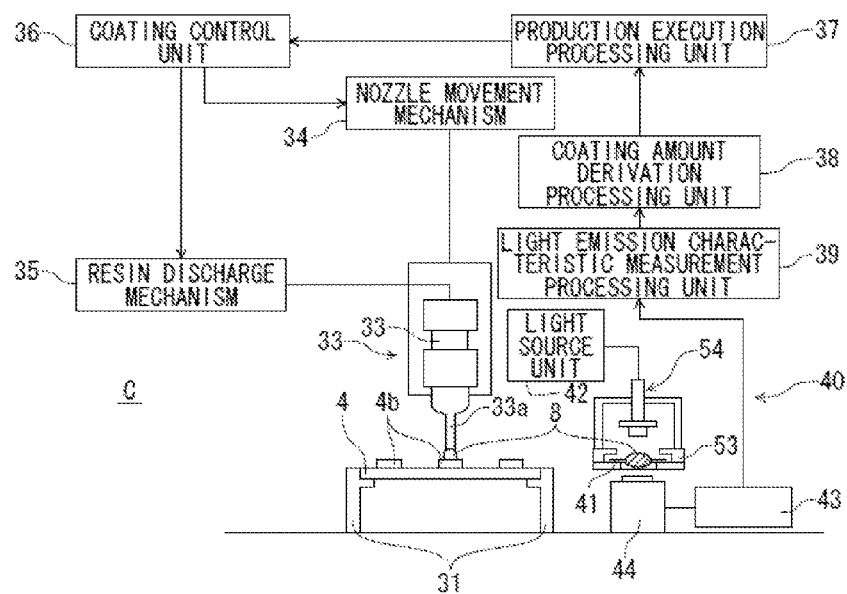

As illustrated in FIG. 7B, the resin discharge head 32 is driven by a nozzle movement mechanism 34, and the nozzle movement mechanism 34 is controlled by a coating control unit 36, to thereby conduct moving operation in the horizontal direction (arrow g indicated in FIG. 7A), and up/down operation. The resin 8 is supplied to the resin discharge head 32 in a state where the resin 8 is stored in a syringe installed in a dispenser 33, and an air pressure is supplied within the dispenser 33 by a resin discharge mechanism 35 so that the resin 8 within the dispenser 33 is discharged through the discharge nozzle 33a, and coated on the LED mounting portions 4b formed on the substrate 4. In this situation, the resin discharge mechanism 35 is controlled by the coating control unit 36, thereby being capable of arbitrarily controlling the discharge amount of the resin 8. That is, the resin coating unit C has a function of discharging the resin 8 with a variable coating amount, and coating the resin 8 at the arbitrary position to be coated. The resin discharge mechanism 35 can employ a variety of liquid discharge systems such as a plunger system using a mechanical cylinder, or a screw pump system aside from the pneumatic dispenser 33.

Figure 9:
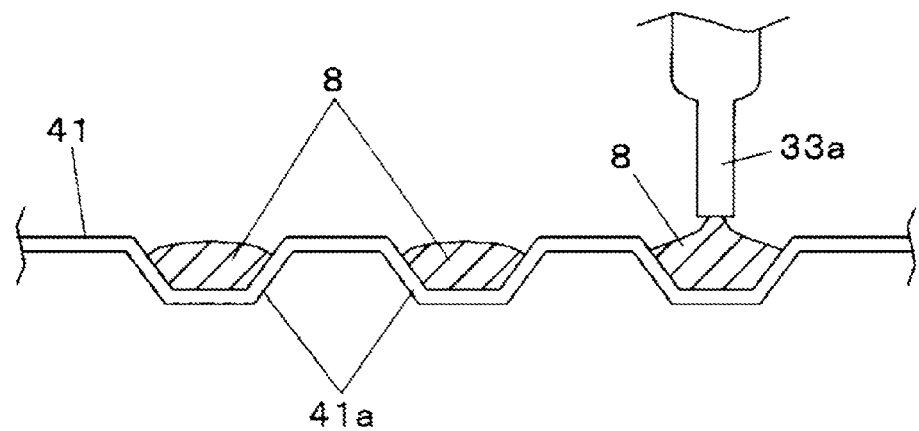
[FIG. 9]

A trial coating/measurement unit 40 is arranged on a side of the substrate transport mechanism 31 so as to be located within a movement range of the resin discharge head 32. The trial coating/measurement unit 40 has a function of determining whether the coating amount of the resin 8 is proper, or not, by measuring the light emission characteristic of the trial coated resin 8, prior to the actual production coating operation for coating the resin 8 on the LED mounting portions 4*b* of the substrate 4. That is, the light emission characteristic when a translucent member 41 that has been trial-coated with the resin 8 by the resin coating unit C is irradiated with a light emitted from a light source unit 42 for measurement is measured by the light emission characteristic measurement portion including a spectrometer 43, an integrating sphere 44, and a light emission characteristic measurement processing unit 39. The measurement result is compared with a preset threshold value to determine whether the preset resin coating amount specified by the resin coating information 14 illustrated in FIG. 4 is proper, or not. In this embodiment, as illustrated in FIG. 9, the translucent member 41 is of an emboss type (emboss tape) in which emboss portions 41*a* corresponding to recess shapes of the LED package PKG are protruded toward a lower surface of a tape material formed of a transparent resin plane sheet-like member.

The resin 8 containing the phosphor grains therein is not always stable in composition and property, and even if the appropriate resin coating amount is set according to the resin coating information 14 in advance, the concentration of the phosphor and the viscosity of resin are not prevented from being varied with time. For that reason, even if the resin 8 is discharged with the discharge parameter corresponding to the preset appropriate resin coating amount, the resin coating amount per se may be varied from the preset appropriate value. Further, even if the resin coating amount per se is proper, the supply amount of phosphor grains to be originally supplied may be varied according to a change in the concentration.

In order to exclude the above disadvantages, in this embodiment, the trial coating for inspecting whether an appropriate supply amount of phosphor grains are supplied at given intervals, or not, is executed by the resin coating device M4. Further, the measurement of the light emission characteristic is executed for the trial coated resin 8, to thereby stabilize the supply amount of the phosphor grains on the basis of the original light emission characteristic. The resin coating unit C provided in the resin coating device M4 according to this embodiment has a function of executing measurement coating processing for trial-coating the resin 8 on the translucent member 41 for the above-mentioned light emission characteristic measurement, and production coating processing for coating the resin 8 on the LED element 5 mounted on the substrate 4 for the actual product, together. The measurement coating processing and the production coating processing are each executed by causing the coating control unit 36 to control the resin coating unit C.

Figure 10:
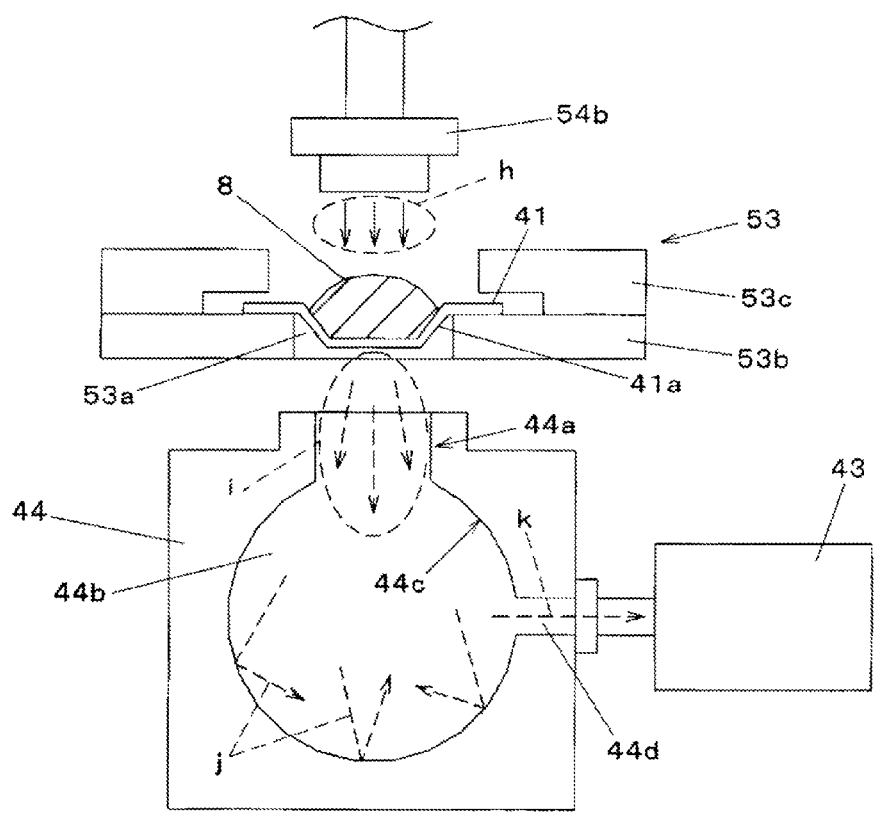
[FIG. 10]

The detailed configuration of the trial coating/measurement unit 40 will be described with reference to FIGS. 8, 9, and 10. As illustrated in those figures, the trial coating/measurement unit 40 includes a supply reel 47 that supplies the translucent member 41 to a base portion 45, a recovery reel 48 that recovers the translucent member 41 supplied by the supply reel 47, and the light source unit 42, spectrometer 43, and the integrating sphere 44 described above. The translucent member 41 between the supply reel 47 and the recovery reel 48 is guided by a plurality of guide pulleys 49, and one tension pulley 50, and pulled (driven) by a sprocket 52 driven by a sprocket drive motor 51 (drive source). As a result, a part of the translucent member 41 passes over an upper surface of a trial coating/stage 40*a* and between a translucent member placement portion 53 and an irradiation portion 54 in the horizontal direction. As illustrated in FIG. 10, the translucent member placement portion 53 is structured to install an upper guide member 53*c* having a function of guiding both end surfaces of the translucent member 41 on an upper surface of a lower support member 53*b* that supports a lower surface of the translucent member 41.

Figure 8:
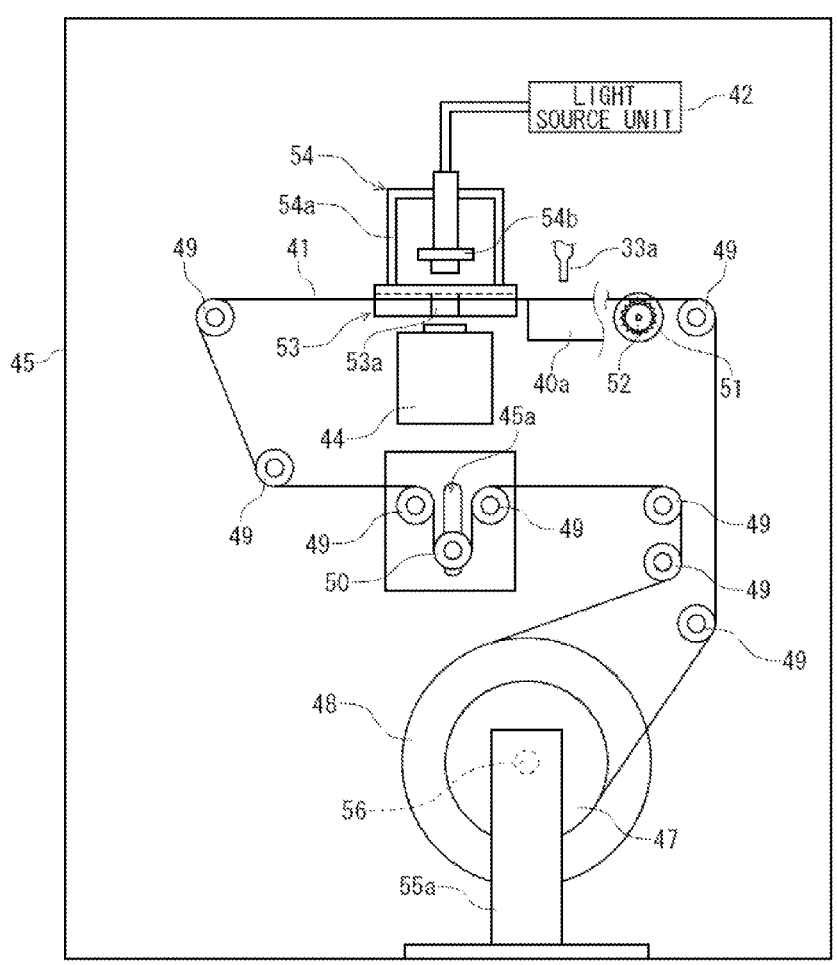
[FIG. 8]

Referring to FIG. 8, the tension pulley 50 is provided in the base portion 45 so as to be movable vertically along a pulley guide 45*a* extended vertically. The tension pulley 50 gives a tension to the translucent member 41 by its weight. This prevents the translucent member 41 from being slacked.

Figure 11:
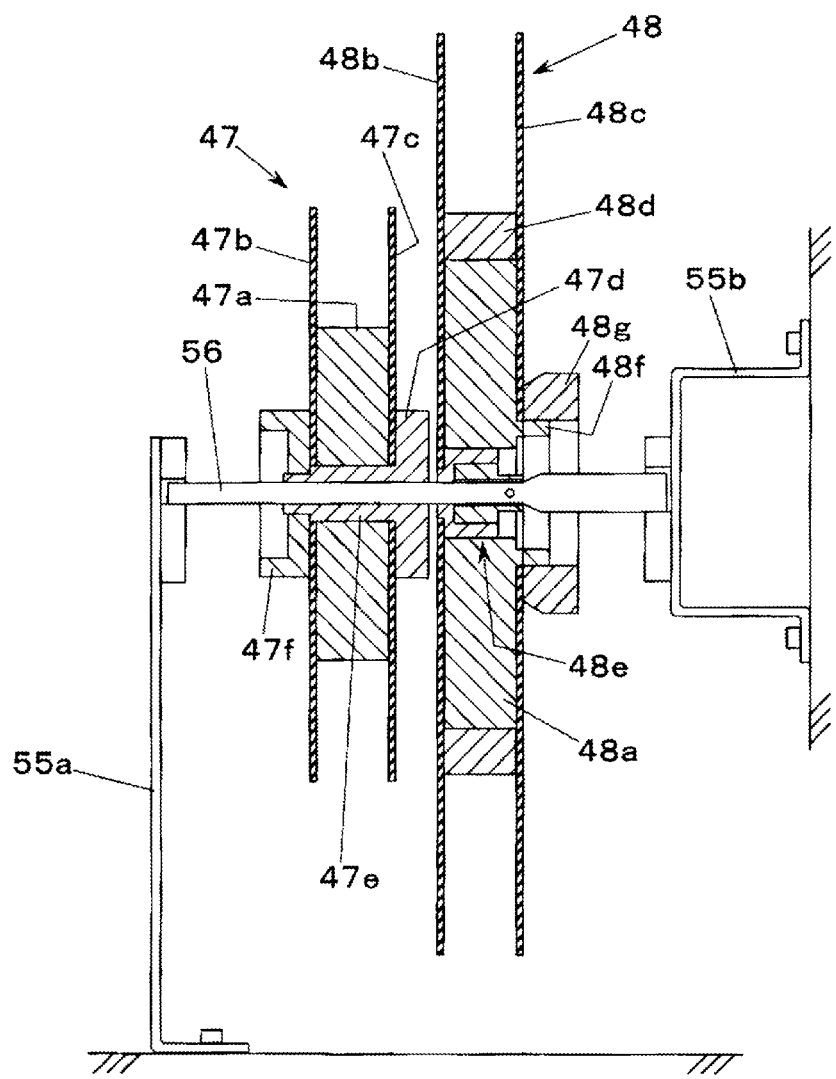
[FIG. 11]
Figure 12:
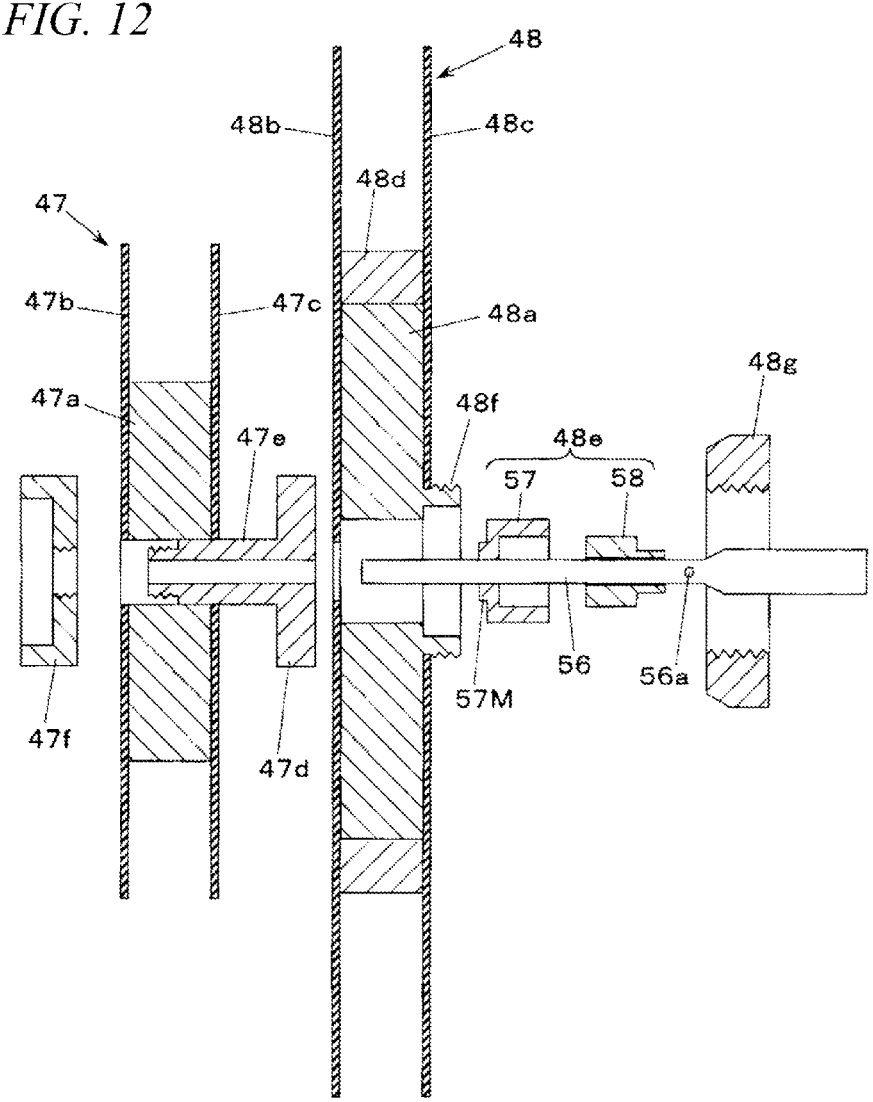
[FIG. 12]

In FIGS. 8, 11, and 12, the supply reel 47 and the recovery reel 48 are arranged coaxially with a support shaft 56 (shaft member) that extends in the horizontal direction, and has both ends rotatably supported by a pair of shaft support members 55*a* and 55*b*.

Referring to FIGS. 11 and 12, the supply reel 47 includes a hollow cylindrical member 47*a* on which the translucent member 41 is wound, and a thin plate disc-shaped first guide member 47*b* that is arranged on one side surface of the cylindrical member 47*a* coaxially with the cylindrical member 47*a*, and fixed to the cylindrical member 47*a*. The supply reel 47 also includes a thin plate disc-shaped second guide member 47*c* that is arranged on the other side surface of the cylindrical member 47*a*, and has the same diameter as that of the first guide member 47*b*. The supply reel 47 further includes a penetration member 47*e* that is disposed to penetrate through the centers of the cylindrical member 47*a*, the first guide member 47*b*, and the second guide member 47*c* from the side of the second guide member 47*c*, and has a flange portion 47*d* formed on an end portion of the second guide member 47*c* side. The supply reel 47 still further includes a tightening member 47*f* that is screwed with the other end of the penetration member 47*e* on the first guide member 47*b* side, and tightens the cylindrical member 47*a*, the first guide member 47*b*, and the second guide member 47*c* in cooperation with the flange portion 47*d* of the penetration member 47*e*. The support shaft 56 is pressed into the penetration member 47*e*.

Referring to FIGS. 11, 12, 13A, and 13B, the recovery reel 48 includes a hollow cylindrical member 48*a* on which the translucent member 41 is wound, and a thin plate disc-shaped first guide member 48*b* that is arranged on one side surface of the cylindrical member 48*a* coaxially with the cylindrical member 48*a*, and fixed to the cylindrical member 48*a*. The recovery reel 48 also includes a thin plate disc-shaped second guide member 48*c* that is arranged on the other side surface of the cylindrical member 48*a*, and has the same diameter as that of the first guide member 48*b*. The recovery reel 48 further includes a translucent member fixing ring 48*d* which is detachably fitted onto an outer peripheral surface of the cylindrical member 48*a*. The recovery reel 48 still further includes a torque limiter 48*e* that is disposed to penetrate through the centers of the cylindrical member 48*a*, the first guide member 48*b*, and the second guide member 48*c* from the side of the second guide member 48*c*. The recovery reel 48 yet still further includes a tightening member 48*g* that is screwed with an outer peripheral surface of a protruding portion 48*f* disposed to protrude from the cylindrical member 48a toward the side of the second guide member 48c, and tightens the second guide member 48c to the cylindrical member 48a.

Figure 13A:
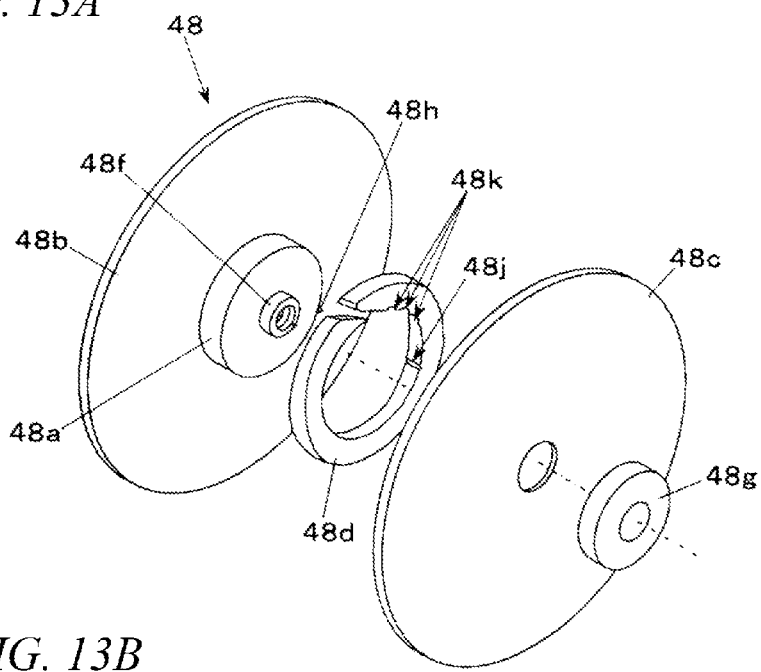
FIGS. 13A and 13B are an exploded perspective view and a side view of a part of the trial coating/measurement unit provided in the LED package manufacturing system according to the embodiment of the present invention.
Figure 13B:
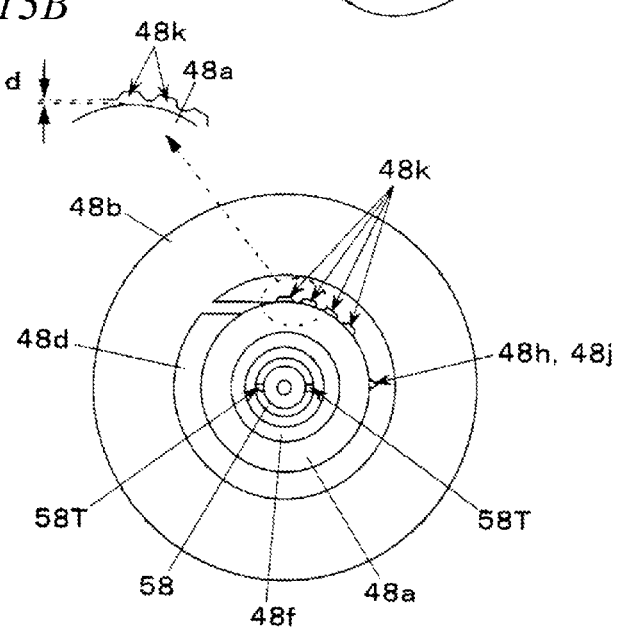
Figure 14A:
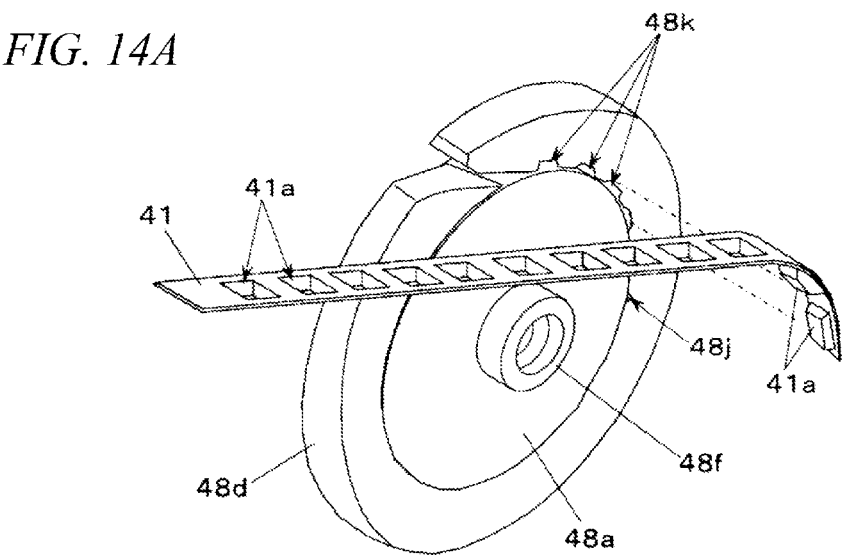
FIGS. 14A and 14B are exploded perspective views of a part of the trial coating/measurement unit provided in the LED package manufacturing system according to the embodiment of the present invention.
Figure 14B:
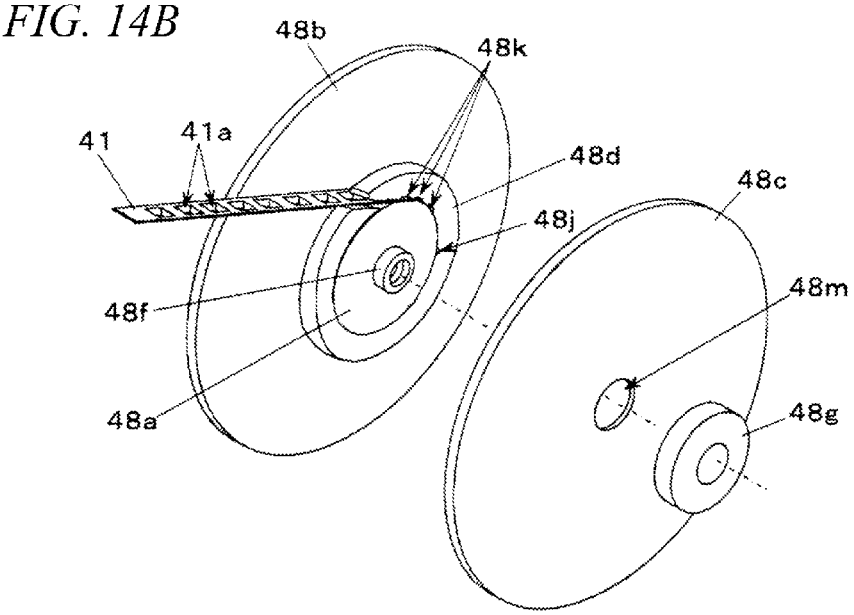

Referring to FIGS. 13A and 13B, the translucent member fixing ring 48d is fitted onto an outside of the cylindrical member 48a. In this situation, a locking projection 48h disposed on the outer peripheral surface of the cylindrical member 48a is inserted into a projection locking groove 48j disposed in an inner peripheral surface of the translucent member fixing ring 48d. With this configuration, the translucent member fixing ring 48d rotates integrally with the cylindrical member 48a when the cylindrical member 48a rotates about the support shaft 56.

Figure 15A:
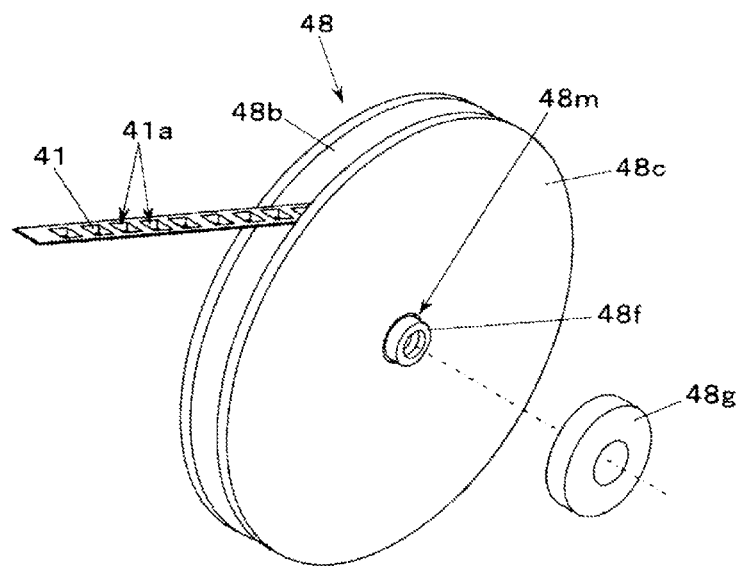
FIGS. 15A and 15B are an exploded perspective view and a perspective view of a part of the trial coating/measurement unit provided in the LED package manufacturing system according to the embodiment of the present invention.
Figure 15B:
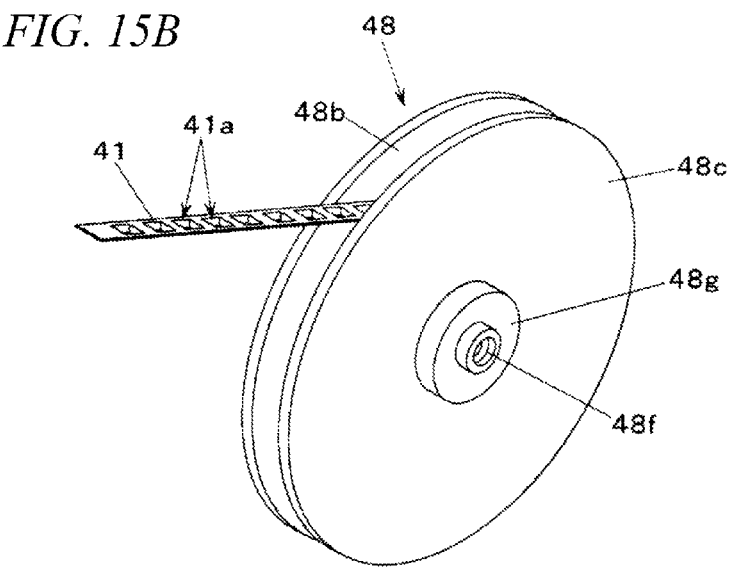

Referring to FIGS. 13A, 13B, 14A, and 14B, a plurality of concave-convex portions 48k configured to reverse an external configuration of an emboss portion 41a of the translucent member 41 are aligned in an inner peripheral surface of the translucent member fixing ring 48d. In a state where the translucent member fixing ring 48d is fitted onto the outer peripheral surface of the cylindrical member 48a, a gap d having a size slightly larger than a thickness of the translucent member 41 is formed between the inner peripheral surface of the translucent member fixing ring 48d and the outer peripheral surface of the cylindrical member 48a (an enlarged diagram illustrated in FIG. 13B). An end portion of the translucent member 41 reeled out of the supply reel 47 is inserted into the gap d. In this situation, the emboss portion 41a of the translucent member 41 is internally pressed along the configuration of the concave-convex portions 48k of the translucent member fixing ring 48d, and blocked by the concave-convex portions 48k (from FIG. 14A to FIG. 14B). As a result, the translucent member 41 is fixed to the recovery reel 48. In this way, after the end portion of the translucent member 41 is inserted between the inner peripheral surface of the translucent member fixing ring 48d and the cylindrical member 48a, the protruding portion 48f of the cylindrical member 48a is penetrated through a hole 48m in the center of the second guide member 48c (from FIG. 14B to FIG. 15A). Thereafter, the tightening member 48g is screwed with the protruding portion 48f of the cylindrical member 48a (FIG. 15B).

Figure 16A:
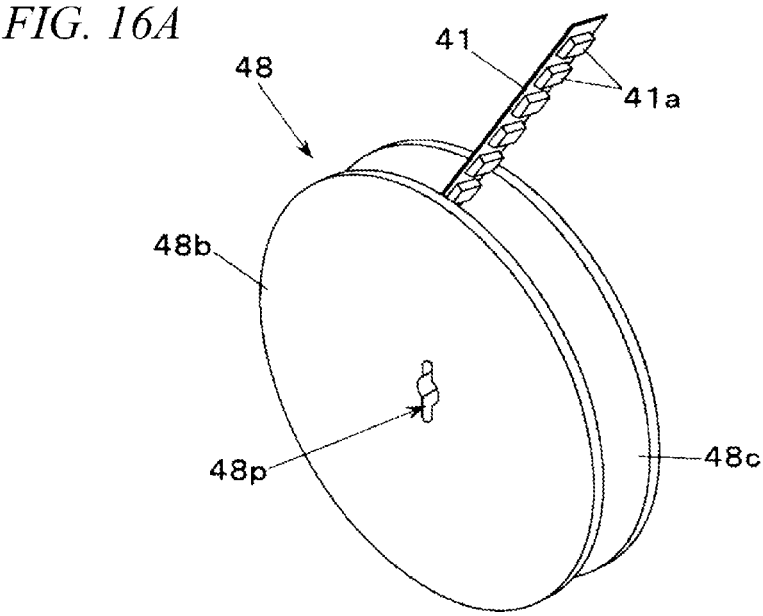
FIGS. 16A and 16B are perspective views of a part of the trial coating/measurement unit provided in the LED package manufacturing system according to the embodiment of the present invention.
Figure 16B:
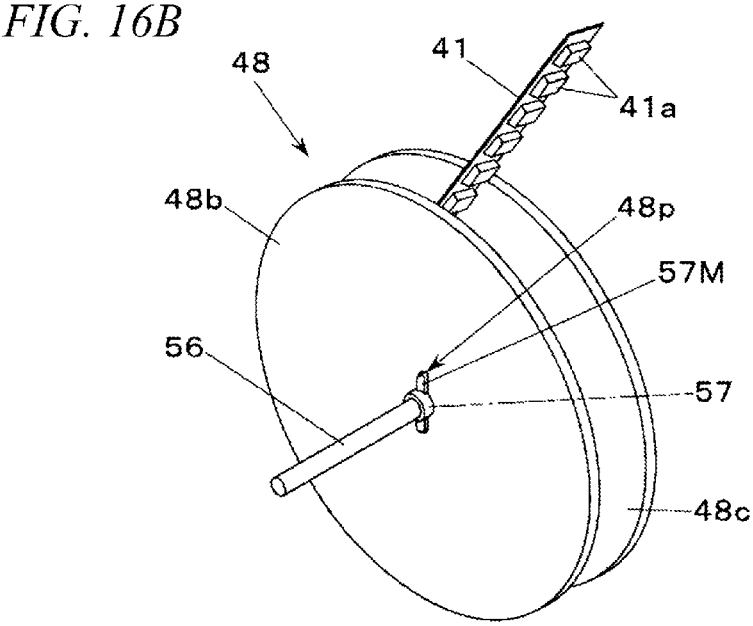
Figure 17A:
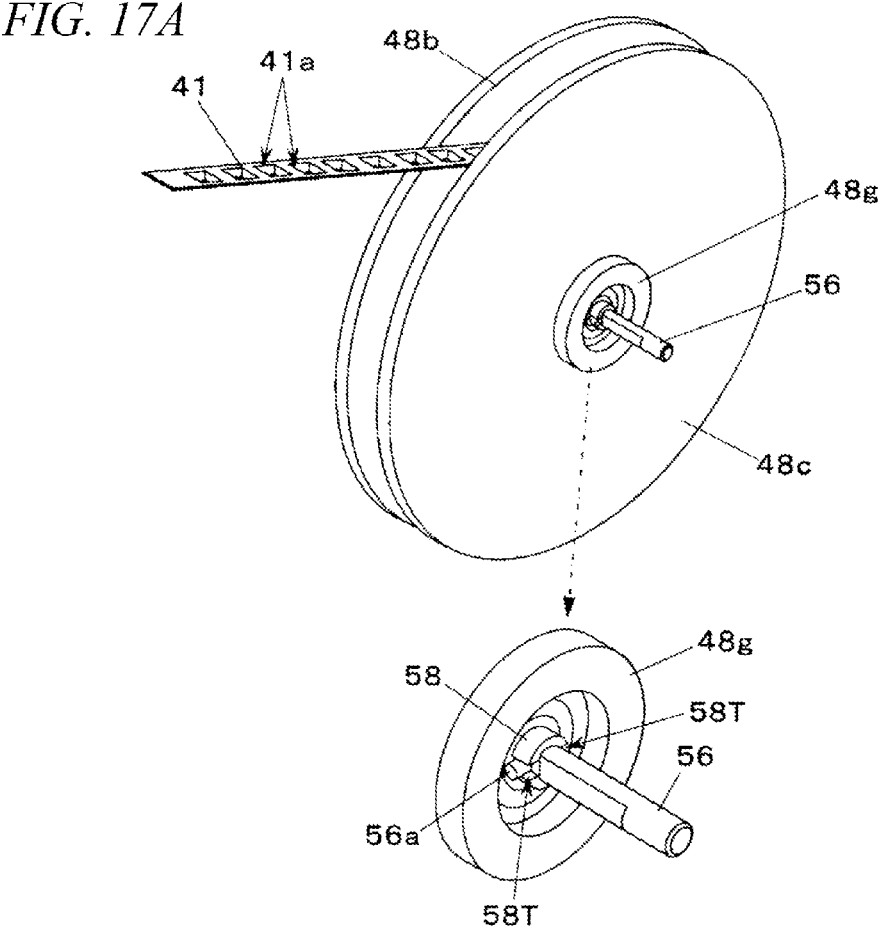
FIGS. 17A and 17B are a perspective view and an enlarged exploded perspective view of a part of the trial coating/measurement unit provided in the LED package manufacturing system according to the embodiment of the present invention.
Figure 17B:
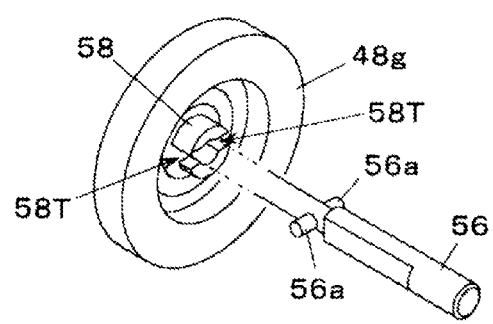

Referring to FIG. 12, the torque limiter 48e includes a reel side member 57 having a hollow cylindrical shape, and a shaft side member 58 that is inserted into the reel side member 57. The reel side member 57 engages a retainer projection 57M (also refer to FIG. 16B) formed on the end portion of the first guide member 48b side with a key groove 48p provided in the center of the first guide member 48b (from FIG. 16A to FIG. 16B). On the other hand, the support shaft 56 penetrates through the shaft side member 58, and two engagement projections 56a (also refer to FIGS. 17A and 17B) disposed on the outer peripheral surface of the support shaft 56 are engaged with two projection engagement portions 58T formed in the shaft side member 58 (FIGS. 17A and 17B). For that reason, when the supply reel 47 rotates, thereby rotating the support shaft 56, the recovery reel 48 rotates about the support shaft 56 by the aid of an internal frictional engagement force (frictional engagement force between the inner peripheral surface of the reel side member 57 and the outer peripheral surface of the shaft side member 58) of the torque limiter 48e. Also, when the recovery reel 48 rotates about the support shaft 56, the support shaft 56 rotates by the aid of the internal frictional engagement force of the torque limiter 48e, to thereby rotate the supply reel 47.

As illustrated in FIGS. 18A to 18F, the translucent member 41 is driven by the sprocket 52 driven by the sprocket drive motor 51, and conducts a forward movement in a direction (arrow W1 indicated in FIGS. 18B, 18D, and 18F) from the supply reel 47 side toward the recovery reel 48 side, and a backward movement in a direction (arrow W2 indicated in FIGS. 18C and 18E) from the recovery reel 48 side toward the supply reel 47 side. Thus, the translucent member 41 is precisely positioned by a rotation control of the sprocket 52. In the forward movement of the translucent member 41, the supply reel 47 rotates together with the support shaft 56 by the translucent member 41 pulled by the sprocket 52, as a result of which the translucent member 41 is reeled out of the supply reel 47. Also, a rotating force of the support shaft 56 is transmitted to the recovery reel 48 through the internal frictional engagement force of the torque limiter 48e to rotate the recovery reel 48 whereby the translucent member 41 that has been moved forward is reeled off, and recovered.

As described above, the torque limiter 48e operates to transmit the rotating force of the supply reel 47 to the recovery reel 48 by the aid of the internal frictional engagement force so as to rotate the recovery reel 48 in the same direction as that of the supply reel 47. However, it is assumed that, in the forward movement of the translucent member 41, a winding radius of the translucent member 41 in the recovery reel 48 is larger than the winding radius of the translucent member 41 in the supply reel 47, and a length of the translucent member 41 reeled off by the recovery reel 48 becomes longer than the length of the translucent member 41 reeled out of the supply reel 47 when the supply reel 47 and the recovery reel 48 rotate at the same rotating angle. In this situation, since the reel side member 57 of the torque limiter 48e and the shaft side member 58 slip on each other (rotating angle of the reel side member 57<rotating angle of the shaft side member 58), there is no case in which an excessive tension is exerted on the translucent member 41, and the translucent member 41 is broken off.

Also, it is assumed that, in the backward movement of the translucent member 41 in which the sprocket 52 rotates backward, the winding radius of the translucent member 41 in the supply reel 47 is larger than the winding radius of the translucent member 41 in the recovery reel 48, and the length of the translucent member 41 reeled off by the supply reel 47 becomes longer than the length of the translucent member 41 reeled out of the recovery reel 48 when the recovery reel 48 and the supply reel 47 rotate at the same rotating angle. Similarly, in this situation, since the reel side member 57 of the torque limiter 48e and the shaft side member 58 slip on each other (rotating angle of the reel side member 57>rotating angle of the shaft side member 58), there is no case in which the translucent member 41 is broken off by the excessive tension.

On the other hand, it is assumed that, in the forward movement of the translucent member 41, the winding radius of the translucent member 41 in the supply reel 47 is larger than the winding radius of the translucent member 41 in the recovery reel 48, and the length of the translucent member 41 reeled out of the supply reel 47 becomes longer than the length of the translucent member 41 reeled off by the recovery reel 48 when the supply reel 47 and the recovery reel 48 rotate at the same rotating angle. In this situation, the reel side member 57 of the torque limiter 48e and the shaft side member 58 rotate at the same rotating angle without any slippage, and a difference in the length of the translucent member 41 is absorbed by a downward movement stroke of the tension pulley 50. As a result, the translucent member 41 is not slacked.

Also, it is assumed that, in the backward movement of the translucent member 41, the winding radius of the translucent member 41 in the recovery reel 48 is larger than the winding radius of the translucent member 41 in the supply reel 47, and the length of the translucent member 41 reeled out of the recovery reel 48 becomes longer than the length of the translucent member 41 reeled off by the supply reel 47 when the supply reel 47 and the recovery reel 48 rotate at the same rotating angle. Similarly, in this situation, the reel side member 57 of the torque limiter 48e and the shaft side member 58 rotate at the same rotating angle without any slippage, and the difference in the length of the translucent member 41 is absorbed by the downward movement stroke of the tension pulley 50. As a result, the translucent member 41 is not slacked.

In this way, in the resin coating device M4 according to this embodiment, the supply reel 47 and the recovery reel 48 are arranged on the identical support shaft 56 (shaft member), and when the translucent member 41 is moved forward by the actuation of the sprocket drive motor 51 which is a drive source that moves the translucent member 41 forward, one of the supply reel 47 and the recovery reel 48 rotates while being pulled by the translucent member 41, and peels out the translucent member 41, and the other reel is rotationally driven through the torque limiter 48e disposed on the support shaft 56 to reel off the translucent member 41.

Referring to FIGS. 7A, 7B, and 8, the irradiation portion 54 has a function of irradiating the translucent member 41 with a measurement light emitted by the light source unit 42, and is configured to arrange a light focusing tool 54b into which the measurement light emitted by the light source unit 42 is guided by a fiber cable, within a light shielding box 54a having a simplified dark box function. The light source unit 42 has a function of emitting the excitation light that excites the phosphor contained in the resin 8. In this embodiment, the light source unit 42 is arranged above the translucent member placement portion 53, and irradiates the translucent member 41 with the measurement light through the light focusing tool 54b from above.

In the process in which the translucent member 41 is fed on the trial coating/measurement unit 40 as described above, the resin 8 is trial-coated on the translucent member 41 by the resin discharge head 32. As illustrated in FIG. 9, the trial coating is conducted by discharging (coating) the resin 8 of the appropriate discharge amount of the specified amount specified by the resin coating information 14 by the discharge nozzle 33a into the emboss portion 41a of the translucent member 41 whose lower surface side is supported by the trial coating/stage 40a.

As will be described later, the resin 8 coated by the trial coating/stage 40a is the trial coating for empirically determining whether the phosphor supply amount is proper for the subject LED element 5, or not. Therefore, when the resin 8 is continuously coated on the translucent member 41 in the same trial coating operation by the resin discharge head 32 at a plurality of points, the resin 8 is coated with the coating amount gradually made different on the basis of the known data indicative of a correlation of the light emission characteristic measurement value and the coating amount.

In this way, the translucent member 41 guided into the light shielding box 54a after having been trial-coated with the resin 8 is irradiated with the white light emitted by the light source unit 42 through the light focusing tool 54b from above. Then, as illustrated in FIG. 10, the light that has penetrated through the resin 8 coated on the translucent member 41 is received by the integrating sphere 44 disposed below the translucent member placement portion 53 through a light transmission opening portion 53a disposed in the translucent member placement portion 53.

Figure 18A:
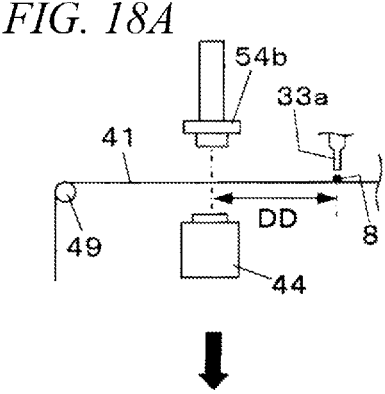
FIGS. 18A to 18F are illustrative views of the operation of the trial coating/measurement unit provided in the LED package manufacturing system according to the embodiment of the present invention.
Figure 18B:
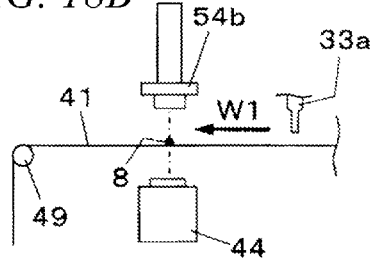
Figure 18C:
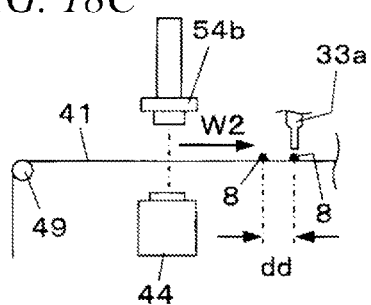
Figure 18D:
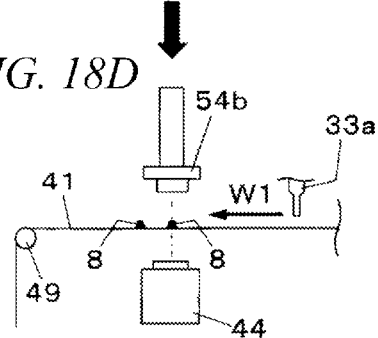
Figure 18E:
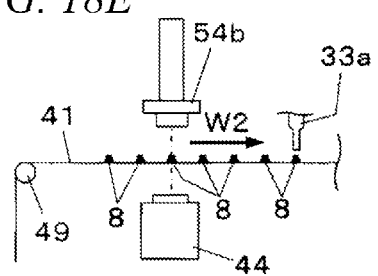
Figure 18F:
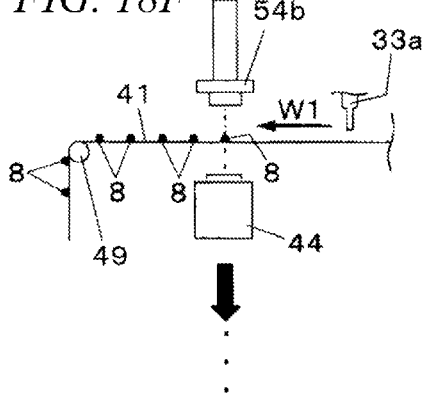
Figure 19A:
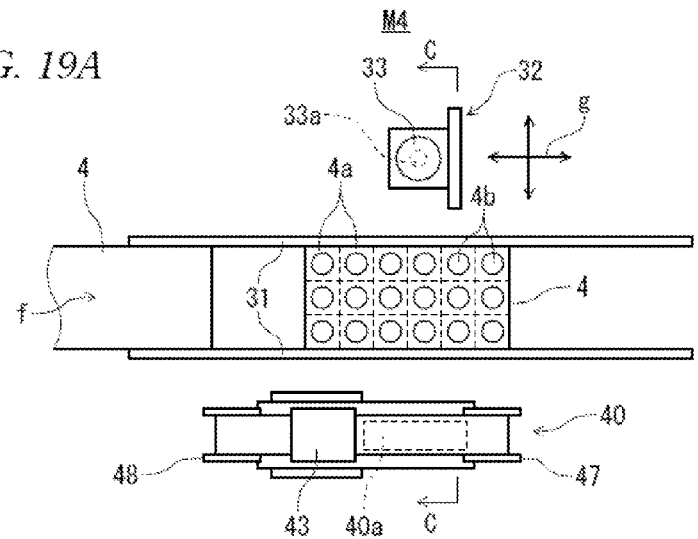
FIGS. 19A and 19B are illustrative views of a configuration and a function of a resin coating device in the LED package manufacturing system according to the embodiment of the present invention.
Figure 19B:
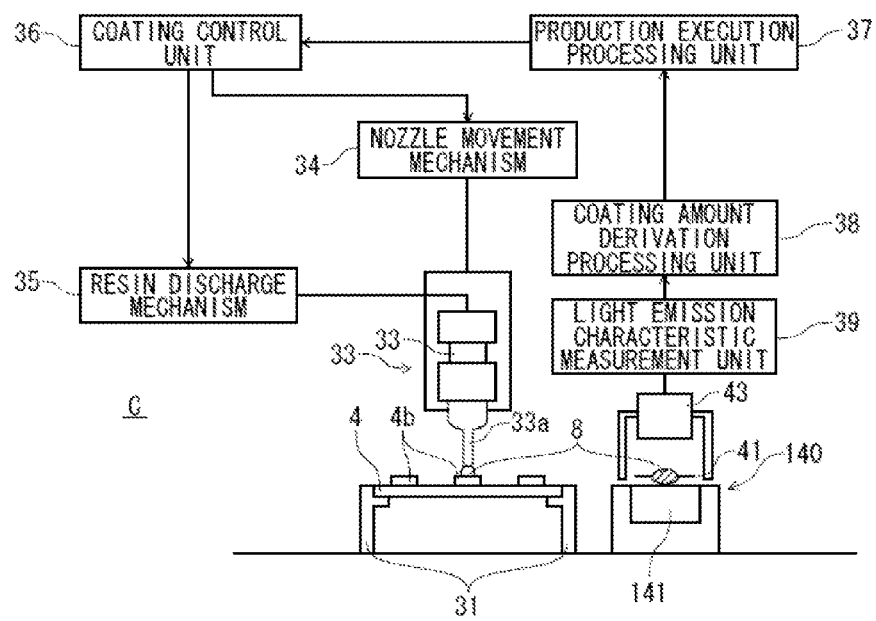

In the trial coating/measurement unit 40, as illustrated in FIGS. 18A and 18C, a distance (distance between the adjacent emboss portions 41a) dd between the resins 8 adjacent in a direction of extending the translucent member 41 on the translucent member 41 is smaller than a distance DD between inspection portions irradiated with the light from the light source unit 42, and supply portions (the dispenser 33 is located immediately above the translucent member 41 when supplying the resin 8 to the translucent member 41) to which the resin 8 is supplied by the dispenser 33. For that reason, the resin 8 coated on the translucent member 41 by the dispenser 33 is moved immediately below the light source unit 42 by allowing the translucent member 41 to be moved forward by the rotating operation of the sprocket 52 (move to left on a paper plane in FIGS. 18A to 18F). In this situation, after the light emission characteristic has been measured, the translucent member 41 is moved backward once for coating the subsequent resin 8. Therefore, in sequentially executing coating of the resin 8 on the translucent member 41, and the inspection of the coated resin 8, the forward movement and the backward movement of the translucent member 41 in the synchronizing operation of the supply reel 47 and the recovery reel 48 are alternately repetitively executed (FIG. 18A→FIG. 18B→ . . . FIG. 18E→FIG. 18F→ . . . ). The translucent member 41 is moved forward bit by bit as a whole while repeating the forward movement and the backward movement, during the execution of the trial coating and the measurement, and a used portion of the translucent member 41 is wound on the recovery reel 48.

Thus, the translucent member 41 is recovered in a state where the translucent member 41 is wound on the recovery reel 48. With this configuration, not only a disposal of the translucent member 41 is easier than that when the translucent member 41 is pushed into a recovery box, or the like as it is (that is, without being wound on the recovery reel 48), but also the forward movement and the backward movement of the translucent member 41 can be smoothly conducted by rotating the recovery reel 48 together with the supply reel 47. Also, the translucent member 41 is attached onto the recovery reel 48 by locking the emboss portion 41a with the translucent member fixing ring 48d detachably fitted to the outer peripheral surface of the cylindrical member 48a disposed in the center of the recovery reel 48. As a result, the attachment of the translucent member 41 onto the recovery reel 48, and the recovery thereof are very easy.

The translucent member placement portion 53 has a function of guiding the translucent member 41 in the transporting operation in the trial coating/measurement unit 40, and placing the translucent member 41 on which the resin 8 has been trial-coated in the measurement coating processing to hold the position. As illustrated in FIG. 10, the integrating sphere 44 has a function of focusing the transmission light that has been applied from the light focusing tool 54b (arrow h), and penetrated through the resin 8, and guiding the light into the spectrometer 43. That is, the integrating sphere 44 has a spherical reflection surface 44c that is spherically shaped therein. The transmission light (arrow i) input from an opening portion 44a located immediately below the light transmission opening portion 53a is input into a reflection space 44b from the opening portion 44a located in a top of the integrating sphere 44. The transmission light is extracted as the measurement light (arrow k) from an output portion 44d in a process of repeating total reflection (arrow j) by a spherical reflection surface 44c, and received by the spectrometer 43.

In the above-mentioned configuration, the resin 8 that has been trial-coated on the translucent member 41 is irradiated with the white light emitted by the LED package PKG used in the light source unit 42. In this process, a blue light component contained in the white light excites the phosphor in the resin 8 to emit a yellow light. Then, the white light in which the yellow light and the blue light are additively mixed together is emitted from the resin 8 toward above, and received by the spectrometer 43 through the above-mentioned integrating sphere 44.

Then, the received white light is analyzed by the light emission characteristic measurement processing unit 39 to measure the light emission characteristic, as illustrated in FIG. 7B. In this case, the light emission characteristics such as a color hue rank of the white color, and the light beam are inspected, and as a result of the inspection result, a deviation from the specified light emission characteristic is detected. The integrating sphere 44, the spectrometer 43, and the light emission characteristic measurement processing unit 39 configure a light emission characteristic measurement portion that receives, from below of the translucent member 41, the light emitted from the resin 8 by irradiating the resin 8 coated on the translucent member 41 with the excitation light (white light emitted from a white LED in this example) emitted by the light source unit 42 from above, and measures the light emission characteristics of the light emitted by the resin 8. In this embodiment, the light emission characteristic measurement portion is configured to arrange the integrating sphere 44 below the translucent member 41, and receive the light emitted by the resin 8 through the opening portion 44a of the integrating sphere 44.

The light emission characteristic measurement portion is configured as described above to obtain advantages described below. That is, in the coating shape of the resin 8 trial-coated on the translucent member 41 illustrated in FIG. 9, since the lower surface side of the resin 8 always comes in contact with an upper surface of the translucent member 41, or a bottom surface of the emboss portion 41a, the lower surface of the resin 8 is always kept to a standard height specified by the translucent member 41. Accordingly, a difference in the height between the lower surface of the resin 8 and the opening portion 44a of the integrating sphere 44 is always kept constant. On the contrary, an upper surface of the resin 8 does not always realize the same fluid level shape/height due to a disturbance such as coating conditions by the discharge nozzle 33a, and an interval between the upper surface of the resin 8 and the light focusing tool 54b is varied.

In this example, let us consider the degree of stabilization compared between the irradiation light with which the upper surface of the resin 8 is irradiated, and the transmission light from the lower surface of the resin 8. The irradiation light with which the resin 8 is irradiated is high in the degree of focusing because the irradiation is made through the light focusing tool 54b, and an influence of the variation in the interval between the upper surface of the resin 8 and the light focusing tool 54b on the light transmission can be ignored. On the contrary, since the transmission light that hat penetrated through the resin 8 is the excitation light obtained by exciting the phosphor within the resin 8, the degree of scattering is high, and an influence of the variation in the distance between the lower surface of the resin 8 and the opening portion 44a on the degree of light taken by the integrating sphere 44 cannot be ignored.

In the trial coating/measurement unit 40 according to this embodiment, the light emitted from the resin 8 by irradiating the resin 8 with the excitation light emitted by the light source unit 42 from above is received by the integrating sphere 44 from below of the translucent member 41. As a result, the light emission characteristic can be stably determined. Further, with the use of the integrating sphere 44, the device can be downsized, and the facility costs can be reduced without need to additionally provide a dark room structure in the light receiving portion.

As illustrated in FIG. 7B, the measurement result of the light emission characteristic measurement processing unit 39 is transmitted to a coating amount derivation processing unit 38. The coating amount derivation processing unit 38 conducts the processing of obtaining a deviation between the measurement result of the light emission characteristic measurement processing unit 39 and the light emission characteristic specified in advance, and deriving the appropriate resin coating amount of the resin 8 to be coated on the LED element 5 as the actual production on the basis of this deviation. A new appropriate discharge amount derived by the coating amount derivation processing unit 38 is transmitted to a production execution processing unit 37, and the production execution processing unit 37 instructs the coating control unit 36 about the appropriate resin coating amount newly derived. As a result, the coating control unit 36 controls the nozzle movement mechanism 34 and the resin discharge mechanism 35, and allows the resin discharge head 32 to execute a production coating processing for coating the resin 8 of the appropriate resin coating amount on the LED element 5 amounted on the substrate 4.

In the production coating processing, the resin 8 of the appropriate resin coating amount specified in the resin coating information 14 is first actually coated, and the light emission characteristic is measured in a state where the resin 8 is uncured. Then, a non-defective product range of the light emission characteristic measurement value when the light emission characteristic is measured for the resin 8 coated in the production coating is set, and the non-defective product is used as a threshold value (refer to threshold value data 81a shown in FIG. 21) of the non-defective/defective determination in the production coating.

That is, in the resin coating method in the LED package manufacturing system according to this embodiment, the white LED is used as the light source unit 42 for measurement of the light emission characteristic. Also, the light emission characteristic obtained by slanting a regular light emission characteristic obtained for the completed product in which the resin 8 coated on the LED element 5 is cured by a difference of the light emission characteristic caused by a state in which the resin 8 is uncured is used as the light emission characteristic specified in advance which is a basis of the threshold value setting for the non-defective/defective determination in the production coating. As a result, the resin coating amount in the resin coating process on the LED element 5 can be controlled on the basis of the regular light emission characteristic of the completed product.

In this embodiment, the LED package PKG that emits the white light is used as the light source unit 42. As a result, the light emission characteristic of the trial-coated resin 8 can be measured by a light having the same characteristic as that of the excitation light emitted in the LED package PKG of the completed product, and the inspection result higher in reliability can be obtained. It is not always essential to use the same LED package PKG as that used for the completed product. In the light emission characteristic measurement, a light source device (for example, a blue LED or a blue laser light source that emits the blue light) that can stably emit the blue light having a given wavelength can be used as a light source unit for inspection. The use of the LED package PKG that emits the white light using the blue LED is advantageous in that the light source device of a stable quality can be selected at the low costs. In this example, the blue light of a given wavelength may be extracted with the use of a band pass filter.

The trial coating/measurement unit 40 having the above configuration may be replaced with a trial coating/measurement unit 140 configured as illustrated in FIGS. 19A, 19B, 20A, and 20B. That is, as illustrated in FIGS. 19A, 19B, 20A, and 20B, the trial coating/measurement unit 140 has an external structure in which a cover portion 140b is arranged above a slender horizontal base 140a. The cover portion 140b is formed with an opening portion 140c, and the opening portion 140c is openable by a slidable (arrow l) coating slide window 140d. A trial-coating stage 145a that supports the translucent member 41 from a lower surface side, a translucent member portion 141 on which the translucent member 41 is placed, and the spectrometer 43 arranged above the translucent member portion 141 are disposed within the trial coating/measurement unit 140.

The translucent member portion 141 includes a light source device that emits the excitation light that excites the phosphor as with the light source unit 42 illustrated in FIG. 8, and the translucent member 41 that has been trial-coated with the resin 8 in the measurement coating processing is irradiated with the excitation light from the lower surface side thereof by the light source device. The translucent member 41 is reeled off and recovered by the supply reel 47 as in the example illustrated in FIG. 8, and transmitted along an upper surface of the trial-coating stage 145a (arrow m). Therefore, the translucent member 41 goes between the translucent member portion 141 and the spectrometer 43, and is reeled off by the recovery reel 48.

In a state where the coating slide window 140d is slid and opened, the upper surface of the trial-coating stage 145a is exposed to above, and the translucent member 41 placed on the upper surface can be trial-coated with the resin 8 by the resin discharge head 32. The trial coating is conducted by discharging the resin 8 of the specified coating amount toward the translucent member 41 whose lower surface side is supported by the trial-coating stage 145a by the discharge nozzle 33a.

Figure 20A:
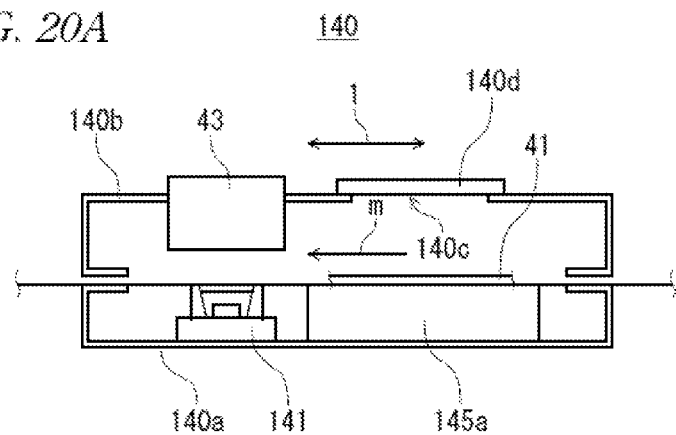
FIGS. 20A and 20B are illustrative views of a light emission characteristic inspection function provided in the resin coating device in the LED package manufacturing system according to the embodiment of the present invention.
Figure 20B:
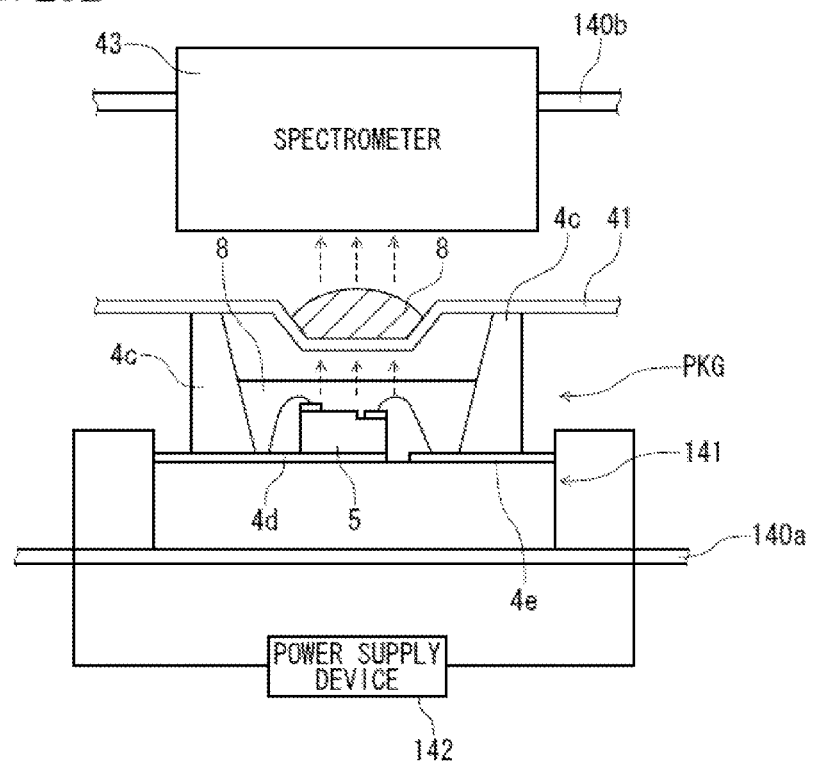

FIG. 20B illustrates a state in which the translucent member 41 that has been trial-coated with the resin 8 in the trial-coating stage 145a is moved, the resin 8 is positioned above the translucent member portion 141, and the cover portion 140b is moved down to form a dark room for the light emission characteristic measurement between the cover portion 140b and the slender horizontal base 140a. In the translucent member portion 141, the LED package PKG that emits the white light is used as the light source device. In the LED package PKG, the wiring layers 4e and 4d connected to the LED element 5 are connected to a power supply device 142. The power supply device 142 turns on to supply an electric power for light emission to the LED element 5 with the result that the LED package PKG emits the white light.

Then, in a process of irradiating the resin 8 that has been trial-coated on the translucent member 41 with the white light that has penetrated through the resin 8, the white light in which the yellow light emitted from the phosphor in the resin 8 excited by the blue light contained in the white light is additively mixed with the blue light is applied from the resin 8 toward above. The spectrometer 43 is arranged above the trial coating/measurement unit 140, and the white light applied from the resin 8 is received by the spectrometer 43, and the received white light is analyzed by the light emission characteristic measurement processing unit 39 to measure the light emission characteristic. In this example, the light emission characteristics such as the color hue rank of the white color, and the light beam are inspected, and as a result of the inspection result, the deviation from the specified light emission characteristic is detected. That is, the light emission characteristic measurement processing unit 39 irradiates the resin 8 coated on the translucent member 41 with the excitation light emitted from the LED element 5 which is the light source unit to measure the light emission characteristic of the light emitted by the resin 8. Then, the measurement result of the light emission characteristic measurement processing unit 39 is transmitted to the coating amount derivation processing unit 38 to execute the same processing as that in the example illustrated in the FIGS. 7A and 7B.

Subsequently, a configuration of a control system in the LED package manufacturing system 1 will be described with reference to FIG. 21. In the management computer 3, the component mounting device M1, and the resin coating device M4 among the components in the respective devices configuring the LED package manufacturing system 1, components related to transmission/reception and updating processing of the element characteristic information 12, the resin coating information 14, the map data 18, and the above-mentioned threshold value data 81a are illustrated.

Figure 21:
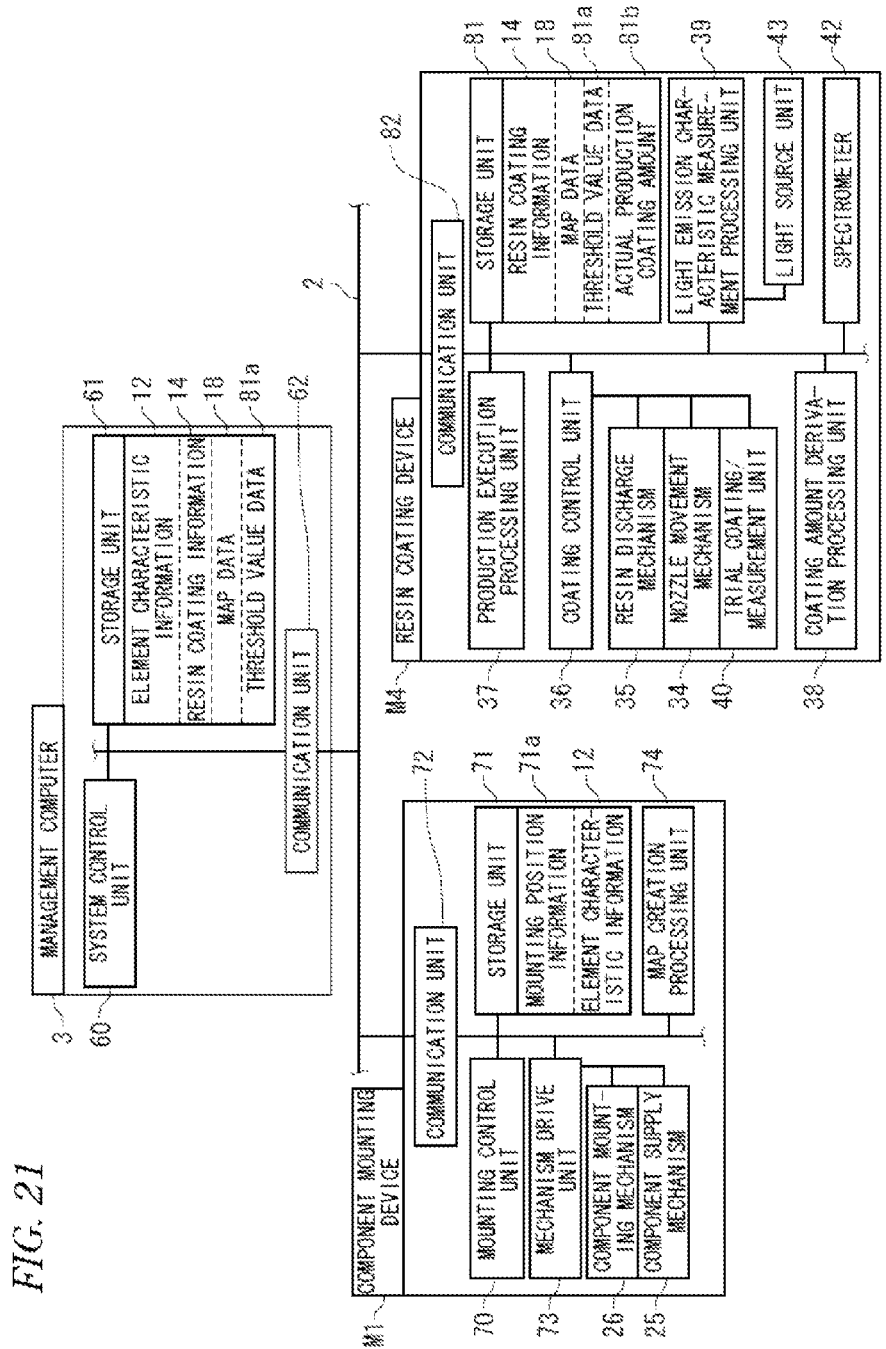
[FIG. 21]

Referring to FIG. 21, the management computer 3 includes a system control unit 60, a storage unit 61, and a communication unit 62. The system control unit 60 overall controls a LED package manufacturing operation by the LED package manufacturing system 1. Programs and data necessary for the control processing by the system control unit 60 as well as the element characteristic information 12, the resin coating information 14, and further the map data 18, and threshold value data 81a as occasion demands are stored in the storage unit 61. The communication unit 62 is connected to another device through the LAN system 2, and transmits and receives control signals and the data. The element characteristic information 12 and the resin coating information 14 are transmitted from the external through the LAN system 2 and the communication unit 62, or through an independent storage medium such as a CD ROM, a USB memory storage, or an SD card.

The component mounting device M1 includes a mounting control unit 70, a storage unit 71, a communication unit 72, a mechanism drive unit 73, and the map creation processing unit 74. In order to allow the component mounting device M1 to execute the component mounting operation, the mounting control unit 70 controls the respective units described below on the basis of a variety of programs and the data stored in the storage unit 71. The storage unit 71 stores the programs and data necessary for the control processing by the mounting control unit 70, as well as the mounting position information 71a and the element characteristic information 12. The mounting position information 71a is created by execution history data of the mounting operation control by the mounting control unit 70. The element characteristic information 12 is transmitted from the management computer 3 through the LAN system 2. The communication unit 72 is connected to another device through the LAN system 2, and transmits and receives the control signals and the data.

The mechanism drive unit 73 is controlled by the mounting control unit 70, and drives the component supply mechanism 25 and the component mounting mechanism 26. As a result, the LED elements 5 are mounted on the respective singulated substrates 4a of the substrate 4. The map creation processing unit 74 (map data creating means) conducts processing of creating the map data 18 that associates the mounting position information 71a stored in the storage unit 71 and indicative of the positions of the LED elements 5 mounted by the component mounting device M1 on the substrate 4 with the element characteristic information 12 on the LED elements 5, for each substrate 4. That is, the map data creating means is disposed in the component mounting device M1, and the map data 18 is transmitted to the resin coating device M4 from the component mounting device M1. The map data 18 may be transmitted from the component mounting device M1 to the resin coating device M4 through the management computer 3. In this case, as illustrated in FIG. 21, the map data 18 is also stored in the storage unit 61 of the management computer 3.

The resin coating device M4 includes the coating control unit 36, a storage unit 81, a communication unit 82, the production execution processing unit 37, the coating amount derivation processing unit 38, and the light emission characteristic measurement processing unit 39. The coating control unit 36 controls the nozzle movement mechanism 34, the resin discharge mechanism 35, and the trial coating/measurement unit 40 configuring the resin coating unit C, to thereby conduct processing of executing the measurement coating processing for trial-coating the translucent member 41 with the resin 8 for the light emission characteristic measurement, and the production coating processing for coating the LED elements 5 with the resin 8 for the actual production.

The storage unit 81 stores the programs and data necessary for the control processing by the coating control unit 36, as well as the resin coating information 14, the map data 18, the threshold value data 81a, and an actual production coating amount 81b therein. The resin coating information 14 is transmitted from the management computer 3 through the LAN system 2, and likewise, the map data 18 is transmitted from the component mounting device M1 through the LAN system 2. The communication unit 82 is connected to another device through the LAN system 2, and transmits and receives the control signals and the data.

The light emission characteristic measurement processing unit 39 conducts processing of irradiating the resin 8 coated on the translucent member 41 with the excitation light emitted from the light source unit 42 to measure the light emission characteristic of the light emitted by the resin. The coating amount derivation processing unit 38 conducts calculation processing of obtaining a deviation between the measurement result of the light emission characteristic measurement processing unit 39, and the light emission characteristic specified in advance, and deriving the appropriate resin coating amount of the resin 8 to be coated on the LED elements 5 for the actual production on the basis of the deviation. Then, the production execution processing unit 37 instructs the coating control unit 36 about the appropriate resin coating amount derived by the coating amount derivation processing unit 38 to execute the production coating processing for coating the LED elements 5 with the resin of the appropriate resin coating amount.

In the configuration illustrated in FIG. 21, processing functions other than the functions for executing the work operation specific to the respective devices, for example, a function of the map creation processing unit 74 installed in the component mounting device M1, and a function of the coating amount derivation processing unit 38 installed in the resin coating device M4 are not always attached to the above devices. For example, the functions of the map creation processing unit 74 and the coating amount derivation processing unit 38 are covered by a calculation processing function provided in the system control unit 60 of the management computer 3, and necessary signal transmission and reception may be conducted through the LAN system 2.

In the configuration of the above-mentioned LED package manufacturing system 1, the component mounting device M1 and the resin coating device M4 are each connected to the LAN system 2. The management computer 3 having the element characteristic information 12 stored in the storage unit 61, and the LAN system 2 configure element characteristic information supply means for supplying information obtained by measuring the light emission characteristics including the light emission wavelengths of the plurality of LED elements 5, individually, in advance, to the component mounting device M1 as the element characteristic information 12. Likewise, the management computer 3 having the resin coating information 14 stored in the storage unit 61, and the LAN system 2 configure resin information supplying means for supplying information that associates the appropriate resin coating amount of the resin 8 for obtaining the LED package PKG having the specified light emission characteristic with the element characteristic information to the resin coating device M4 as the resin coating information.

That is, the element characteristic information supply means for supplying the element characteristic information 12 to the component mounting device M1, and the resin information supplying means for supplying the resin coating information 14 to the resin coating device M4 are configured to transmit the element characteristic information and the resin coating information read from the storage unit 61 of the management computer 3, which is external storage means, to the component mounting device M1 and the resin coating device M4 through the LAN system 2, respectively.

Figure 22:
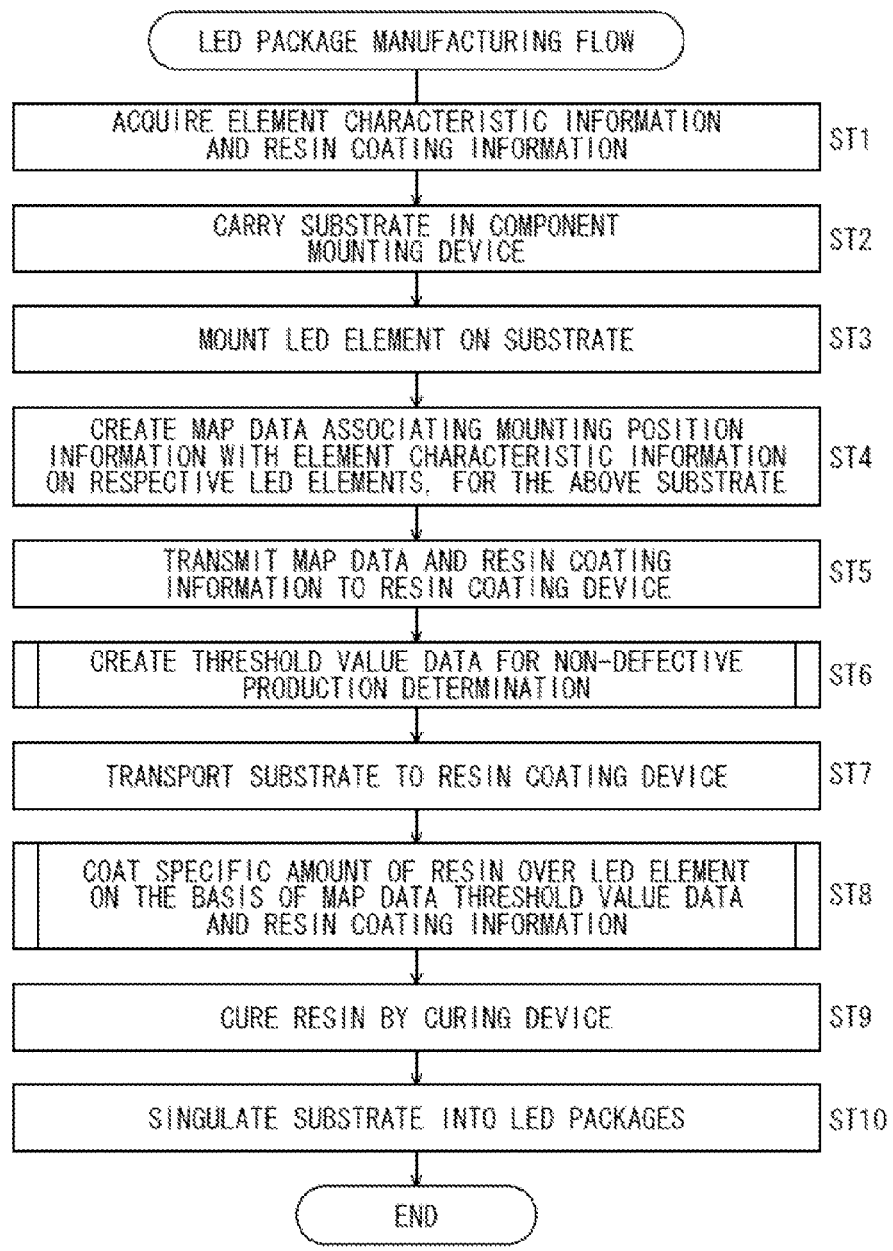
[FIG. 22]

Subsequently, the LED package manufacturing process executed by the LED package manufacturing system 1 will be described along a flow of FIG. 22 with reference to the respective drawings. First, the element characteristic information 12 and the resin coating information 14 are acquired (ST1). That is, the element characteristic information 12 obtained by measuring the light emission characteristics including the light emission wavelengths of the plurality of LED elements 5, individually, in advance, and the resin coating information 14 that associates the appropriate resin coating amount of the resin 8 for obtaining the LED package PKG having the specified light emission characteristic with the element characteristic information 12, are acquired from the external device through the LAN system 2, or through the storage medium.

Figure 28A:
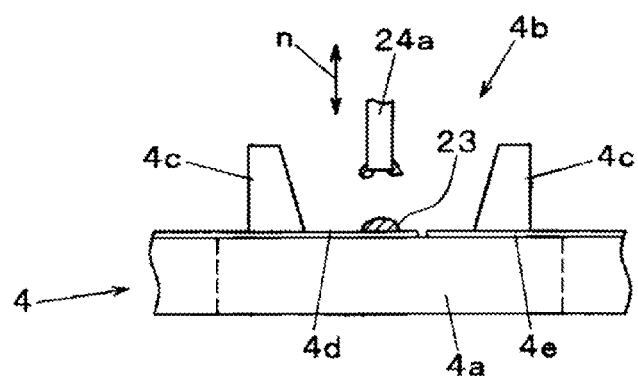
FIGS. 28A to 28D are illustrative views illustrating steps of the LED package manufacturing process by the LED package manufacturing system according to the embodiment of the present invention.
Figure 28B:
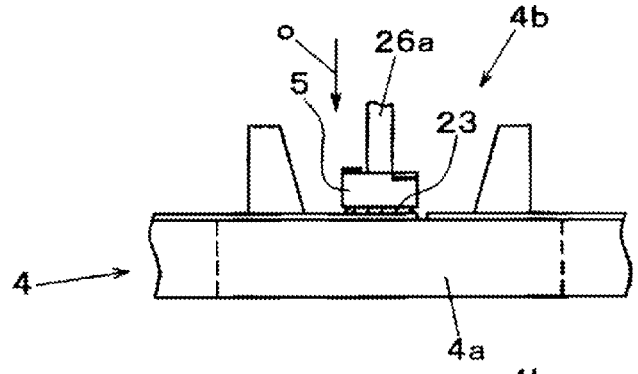

Thereafter, the substrate 4 to be mounted is carried in the component mounting device M1 (ST2). Then, as illustrated in FIG. 28A, the transfer pin 24a of the adhesive transfer mechanism 24 is moved up and down (arrow n) to supply the resin adhesive 23 to the element mounting position within the LED mounting portion 4b. Thereafter, as illustrated in FIG. 28B, the LED element 5 held by the mounting nozzle 26a of the component mounting mechanism 26 is moved down (arrow o), and mounted within the LED mounting portion 4b of the substrate 4 through the resin adhesive 23 (ST3). Then, the map data 18 that associates the mounting position information 71a with the element characteristic information 12 of the respective LED elements 5 is created for the substrate 4 according to execution data of the component mounting operation by the map creation processing unit 74 (ST4). Then, the map data 18 is transmitted from the component mounting device M1 to the resin coating device M4, and the resin coating information 14 is transmitted from the management computer 3 to the resin coating device M4 (ST5). As a result, the resin coating operation can be executed by the resin coating device M4.

Figure 28C:
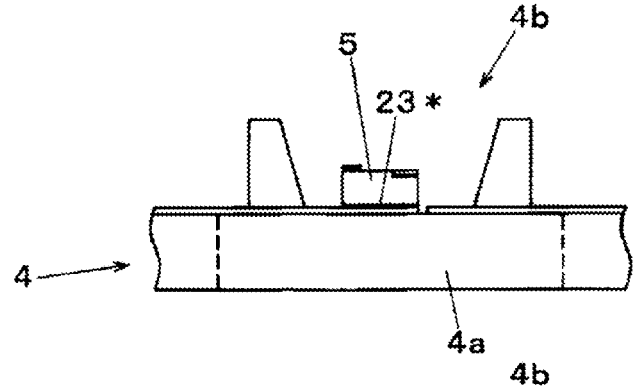
Figure 28D:
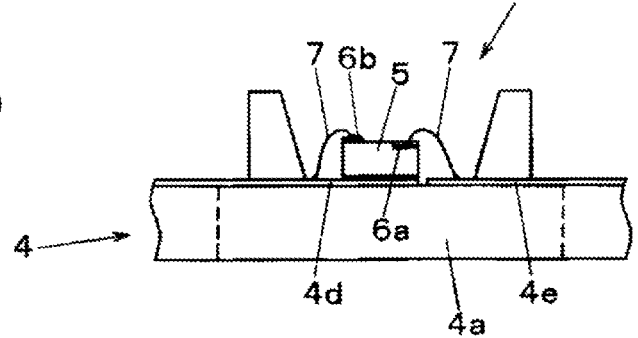

Then, the substrate 4 on which the component has been mounted is transported to the curing device M2, and heated, as a result of which, as illustrated in FIG. 28C, the resin adhesive 23 is thermally cured into a resin adhesive 23*, and the LED elements 5 are adhered to the singulated substrates 4a. Subsequently, the substrate 4 after the resin has been cured is transported to the wire bonding device M3, and as illustrated in FIG. 28D, the wiring layers 4e and 4d of the singulated substrates 4a are connected to the n-type portion electrode 6a and the p-type portion electrode 6b of the LED element 5 by the bonding wires 7.

Figure 23:
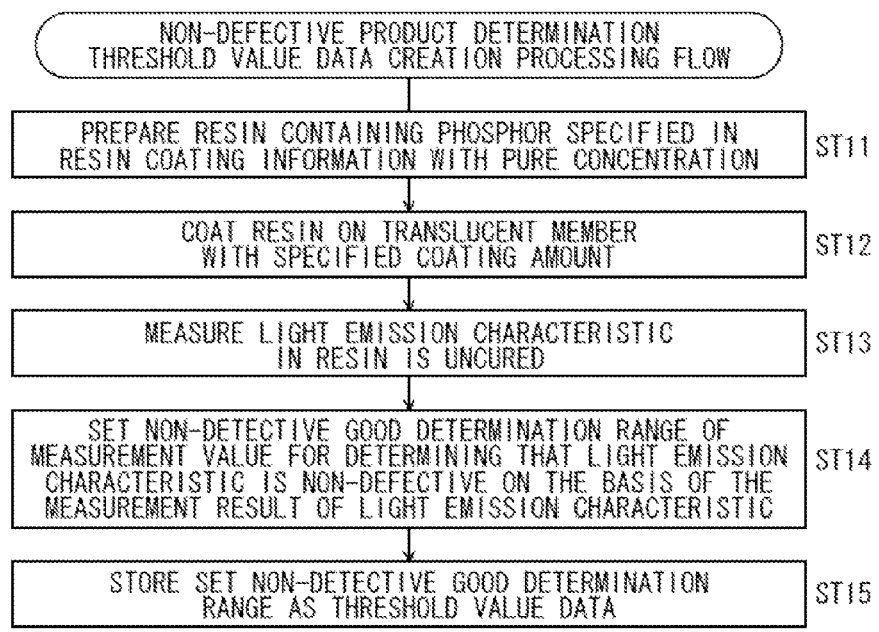
[FIG. 23]
Figure 25:
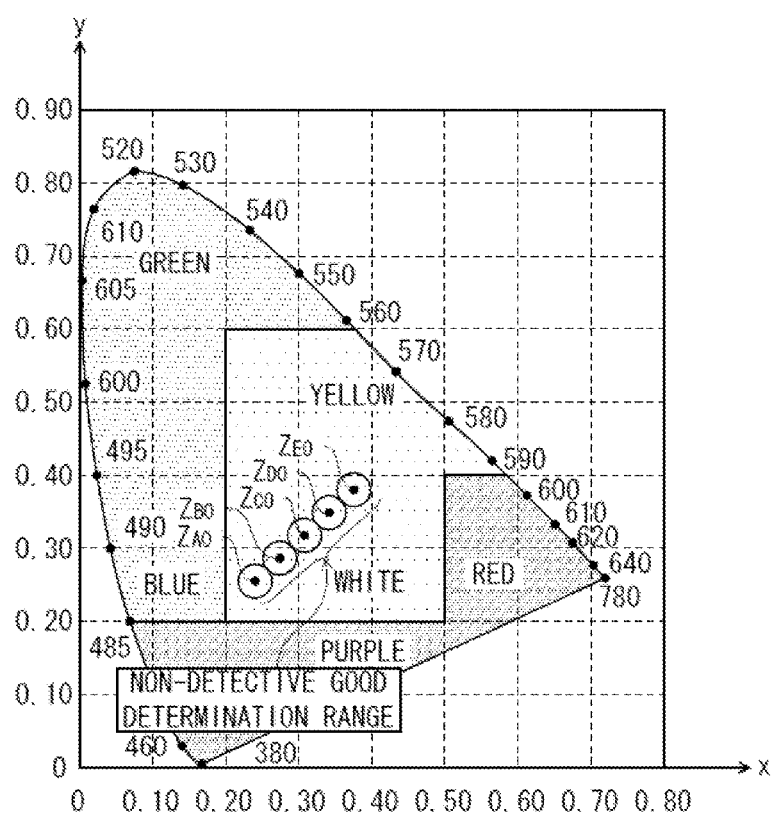
[FIG. 25]

Then, the threshold value data creation processing for the non-defective product determination is executed (ST5). This processing is executed to set the threshold value (refer to the threshold value data 81a illustrated in FIG. 21) for the non-defective/defective determination in the production coating, and the respective production coatings corresponding to the Bin codes [1], [2], [3], [4], and [5] are repetitively executed. The details of the threshold value data creation processing will be described with reference to FIGS. 23, 24A to 24C, and 25. Referring to FIG. 23, the resin 8 containing the phosphor specified in the resin coating information 14 with a pure concentration is prepared (ST11). Then, after the resin 8 has been set in the resin discharge head 32, the resin discharge head 32 is moved to the trial coating/stage 40a of the trial coating/measurement unit 40, and the resin 8 is coated on the translucent member 41 with the specified coating amount (appropriate resin coating amount) indicated in the resin coating information 14 (ST12). Then, the resin 8 coated on the translucent member 41 is moved onto the translucent member placement portion 53, the LED element 5 is allowed to emit the light, and the light emission characteristic in a state where the resin 8 is uncured is measured by the light emission characteristic measurement portion configured as described above (ST13). Then, the non-defective product determination range of the measurement value for determining that the light emission characteristic is non-defective is set on the basis of a light emission characteristic measurement value 39a which is the measurement result of the light emission characteristics measured by the light emission characteristic measurement portion (ST14). The set non-defective product determination range is stored in the storage unit 81 as the threshold value data 81a, and also transferred to the management computer 3 and stored in the storage unit 61 (ST15).

FIGS. 24A to 24C illustrate the threshold value data thus created, that is, the light emission characteristic measurement values obtained in the resin uncured state after the resin 8 containing the phosphor with the pure content has been coated, and the non-defective product determination ranges (threshold values) of the measurement values for determining that the light emission characteristic is non-defective. FIGS. 24A, 24B, and 24C illustrate the threshold values corresponding to the Bin codes [1], [2], [3], [4], and [5] when the phosphor concentrations in the resin 8 are 5%, 10%, and 15%, respectively.

For example, as illustrated in FIG. 24A, when the phosphor concentration of the resin 8 is 5%, the respective coating amounts in the appropriate resin coating amount 15(1) correspond to the respective Bin codes 12b, and the measurement results obtained by measuring the light emission characteristics of the light emitted from the resin 8 by irradiating the resin 8 coated with the respective coating amounts with the blue light of the LED element 5 by the light emission characteristic measurement portion are shown in the light emission characteristic measurement value 39a(1). The threshold value data 81a(1) is set on the basis of the respective light emission characteristic measurement values 39a(1). For example, the measurement result obtained by measuring the light emission characteristic of the resin 8 coated with an appropriate resin coating amount VA0 in correspondence with the Bin code [1] is represented by chromaticity coordinates ZA0 ($X_{A0}$, $Y_{A0}$) on a chromaticity table illustrated in FIG. 25. Given ranges (for example, ±10%) of an X-coordinate and a Y-coordinate on the chromaticity table with the chromaticity coordinates as a center are set as the non-defective product determination range (threshold value). Likewise, in the appropriate resin coating amounts corresponding to the other Bin codes [2] to [5], the non-defective product determination ranges (threshold values) are set on the basis of the light emission characteristic measurement results (refer to chromaticity coordinates ZB0 to ZE0 on the chromaticity table illustrated in FIG. 25). In this example, a given range set as the threshold value is appropriately set according to a precision level of the light emission characteristic obtained in the LED package PKG as the product.

Likewise, FIGS. 24A and 24B illustrate the light emission characteristic measurement values and the non-detective good determination ranges (threshold values) when the respective phosphor concentrations of the resin 8 are 10% an 15%. Referring to FIGS. 24B and 24C, an appropriate resin coating amount 15(2) and an appropriate resin coating amount 15(3) represent the appropriate resin coating amounts when the respective phosphor concentrations are 10%, and 15%. A light emission characteristic measurement value 39a(2) and a light emission characteristic measurement value 39a(3) represent the light emission specific measurement values when the respective phosphor concentrations are 10% and 15%, and a threshold value data 81a(2) and a threshold value data 81a(3) represent the non-detective good determination ranges (threshold values) in the respective cases. The threshold value data created in this manner is selectively used according to the Bin code 12b to which the subject LED element 5 belongs, in the production coating operation. The threshold value data creation processing shown in (ST6) is executed as offline operation by an independent inspection device provided separately from the LED package manufacturing system 1, and data stored as the threshold value data 81a in the management computer 3 in advance may be transmitted to the resin coating device M4 through the LAN system 2, and used.

Figure 29A:
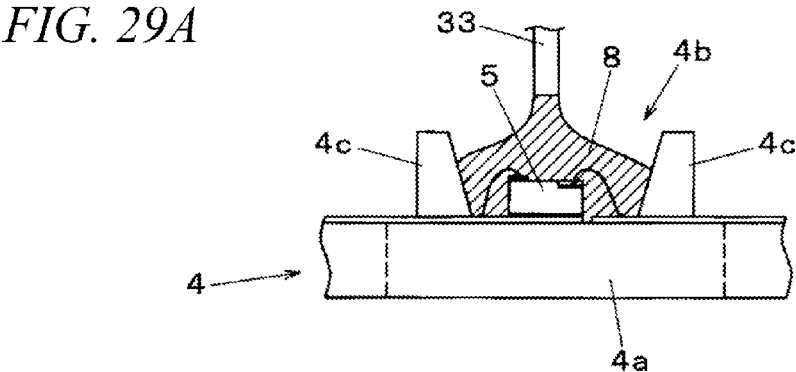
FIGS. 29A to 29D are illustrative views illustrating steps of the LED package manufacturing process by the LED package manufacturing system according to the embodiment of the present invention.
Figure 29B:
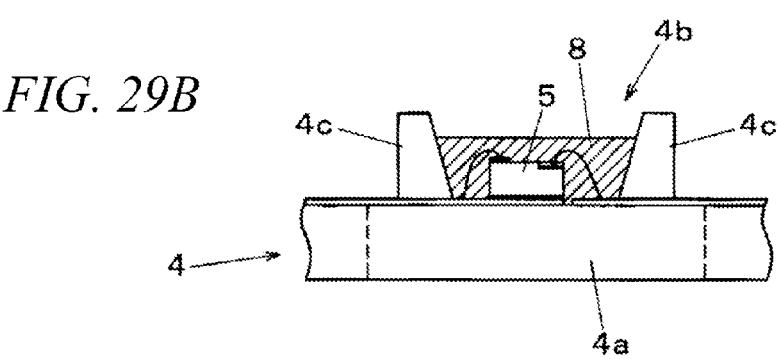

Thereafter, the substrate 4 after the wire bonding has been executed is transported to the resin coating device M4 (ST7), and as illustrated in FIG. 29A, the resin 8 is discharged from the discharge nozzle 33a into the LED mounting portion 4b surrounded by the reflection portion 4c. In this example, the operation of coating the resin 8 of the specific amount illustrated in FIG. 29B over the LED element 5 is executed on the basis of the map data 18, the threshold value data 81a, and the resin coating information 14 (ST8). The details of the resin coating operation processing will be described with reference to FIGS. 24A to 24C, and 25. First, in starting the resin coating operation, a resin container is exchanged as occasion demands (ST21). That is, the dispenser 33 loaded in the resin discharge head 32 is replaced with the dispenser that contains the resin 8 of the phosphor concentration selected according to the characteristic of the LED element 5.

Then, the resin 8 is trial-coated on the translucent member 41 as the light emission characteristic measurement by the resin coating unit C (measurement coating process) (ST22). That is, the resin 8 of the appropriate resin coating amounts (VA0 to VE0) for the respective Bin codes 12b specified in FIG. 4 is coated on the translucent member 41 pulled out to the trial coating/stage 40a by the trial coating/measurement unit 40. In this situation, even if the resin discharge mechanism 35 is instructed about the discharge operation corresponding to the appropriate resin coating amounts (VA0 to VE0), an actual resin coating amount discharged from the discharge nozzle 33a and coated on the translucent member 41 does not always match the above-mentioned appropriate resin coating amount due to a temporal variation in the property of the resin 8, and the actual resin coating amount becomes VA1 to VE1 somewhat different from VA0 to VE0, as illustrated in FIG. 27A.

Then, the translucent member 41 is transmitted in the trial coating/measurement unit 40 whereby the translucent member 41 that has been trial-coated with the resin 8 is transported, and placed on the translucent member placement portion 53 (translucent member placement process). Then, the excitation light that excites the phosphor is emitted from the light source unit 42 arranged above the translucent member placement portion 53 (excitation light emitting process). Then, the resin 8 coated on the translucent member 41 is irradiated with the excitation light from above, as a result of which the light emitted by the resin 8 is received by the spectrometer 43 through the integrating sphere 44 from below the translucent member 41, and the light emission characteristic of the light is measured by the light emission characteristic measurement processing unit 39 (light emission characteristic measuring process) (ST23).

As a result, as illustrated in FIG. 27B, the light emission characteristic measurement value expressed by the chromaticity coordinates Z (refer to FIG. 25) is obtained. The measurement results do not always match the light emission characteristic specified in advance, that is, the standard chromaticity coordinates ZA0 to ZE0 in the appropriate resin coating operation illustrated in FIG. 24A, due to an error in the above-mentioned coating amount, and a change in the concentration of the phosphor grains in the resin 8. For that reason, deviations ($\Delta X_A$, $\Delta Y_A$) to ($\Delta X_E$, $\Delta Y_E$) indicative of distances in the X, and Y coordinates between the obtained chromaticity coordinates ZA1 to ZE1, and the standard chromaticity coordinates ZA0 to ZE0 in the appropriate resin coating operation illustrated in FIG. 24A are obtained to determines whether a correction for obtaining a desired light emission characteristic is necessary, or not.

In this example, it is determined whether the measurement result falls within the threshold value, or not (ST24), and as illustrated in FIG. 27C, the deviation obtained in (ST23) is compared with the threshold value to determine whether the deviations ($\Delta X_A$, $\Delta Y_A$) to ($\Delta X_E$, $\Delta Y_E$) fall within ±10% of ZA0 to ZE0, or not. In this example, if the deviations fall within the threshold value, the discharge operation parameters corresponding to the preset appropriate resin coating amounts VA0 to VE0 are maintained as they are. On the contrary, if the deviations exceed the threshold value, the coating amount is corrected (ST25). That is, the deviations between the measurement results in the light emission characteristic measurement process and the light emission characteristic specified in advance are obtained, and as illustrated in FIG. 27D, the processing for deriving the new appropriate resin coating amounts (AV2 to VE2) for actual production to be coated on the LED elements 5 on the basis of the obtained deviations is executed by the coating amount derivation processing unit 38 (coating amount deriving processing process).

In this example, the corrected appropriate resin coating amounts (VA2 to VE2) are updated values obtained by adding corrections corresponding to the respective deviations to the preset appropriate resin coating amounts VA0 to VE0. Relationships between the deviations and the corrections are recorded in the resin coating information 14 as known associated data in advance. Then, the processing of (ST22), (ST23), (ST24), and (ST25) is repetitively executed on the basis of the corrected appropriate resin coating amounts (VA2 to VE2), and that the deviation between the measurement result and the light emission characteristic specified in advance falls within the threshold value is confirmed in (ST24) to determine the appropriate resin coating amount for the actual production. That is, in the above-mentioned resin coating method, the measurement coating process, the translucent member placement process, the excitation light emitting process, the light emission characteristic measurement process, and the coating amount derivation process are repetitively executed to determinately derive the appropriate resin coating amount. Then, the determined appropriate resin coating amount is stored in the storage unit 81 as the actual production coating amount 81b.

Figure 26:
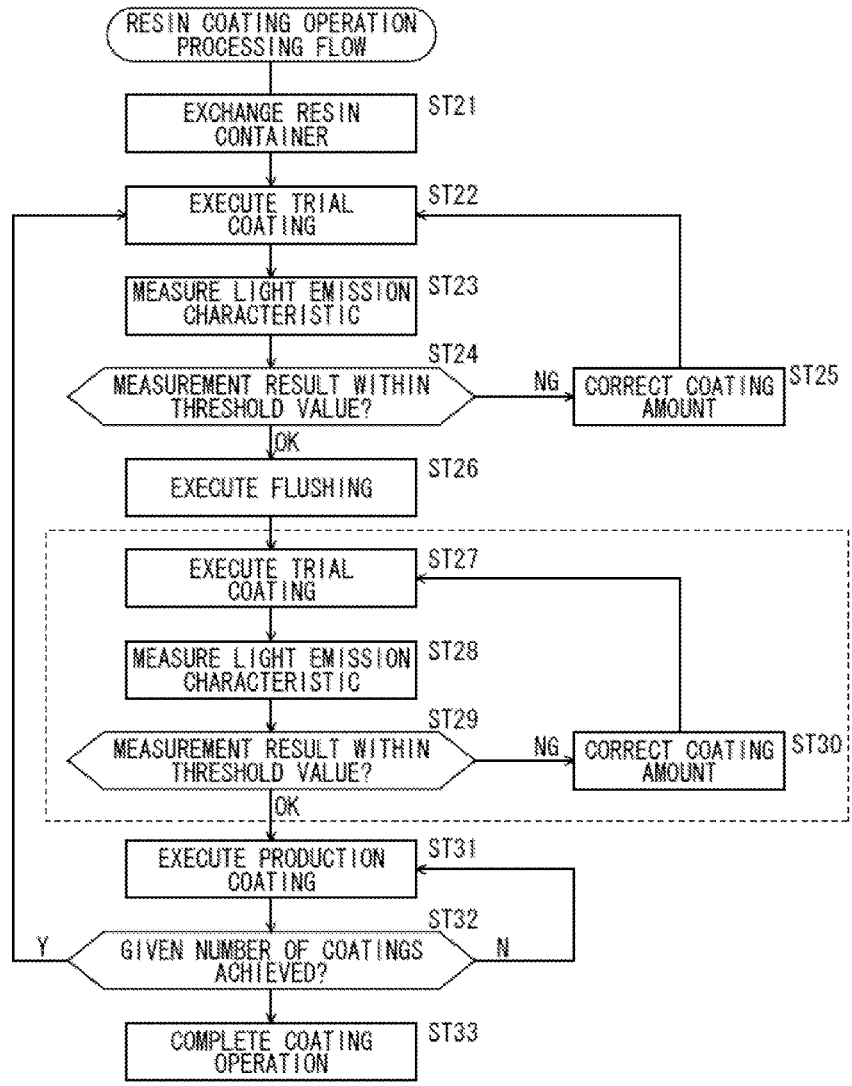
[FIG. 26]

Thereafter, the flow proceeds to a next step to execute flushing (ST26). In this situation, a given amount of resin 8 is discharged from the discharge nozzle 33a to improve a resin flow state within the resin discharge path, and stabilize the operation of the dispenser 33 and the resin discharge mechanism 35. The processing of (ST27), (ST28), (ST29), and (ST30) indicated by a dashed box in FIG. 26 is the same as the processing contents shown in (ST22), (ST23), (ST24), and (ST25), and executed when there is a need to carefully confirm that the desired light emission characteristic is completely ensured, which is not always essential to execute.

If the appropriate resin coating amount providing the desired light emission characteristic is determined with the above processing, the production coating is executed (ST31). That is, the production execution processing unit 37 instructs the coating control unit 36 that controls the resin discharge mechanism 35 about the appropriate resin coating amount derived by the coating amount derivation processing unit 38 and stored as the actual production coating amount 81b, to thereby execute the production coating process for coating the resin 8 of the appropriate resin coating amount on the LED elements 5 mounted on the substrate 4 (production execution process).

Then, in the process of repetitively executing the production coating process, the number of coatings by the dispenser 33 is counted, and it is monitored whether the number of coatings arrives at a preset given number of times, or not (ST32). It is determined that a change in the property of the resin 8 and the phosphor concentration is small until the number of coatings arrives at the given number of times, and the production coating execution (ST31) is repeated while maintaining the same actual production coating amount 81b. Then, if the arrival of the given number of times is confirmed (ST32), it is determined that there is a possibility that the property of the resin 8 and the phosphor concentration are changed (ST22), and the flow returns to (ST22). Thereafter, the same measurement of the light emission characteristic, and the coating amount correction processing based on the measurement result are repetitively executed.

Figure 29C:
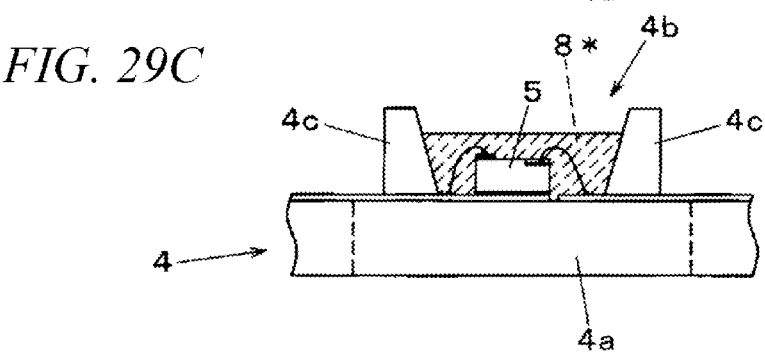
Figure 29D:
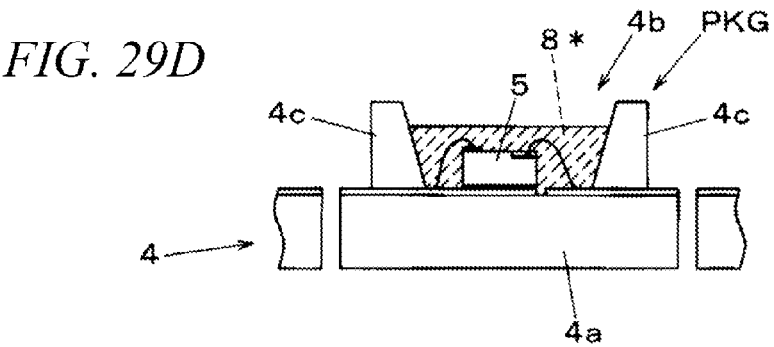

Upon completion of the resin coating for a single substrate 4 in this way, the substrate 4 is transported to the curing device M5, and heated by the curing device M5 to cure the resin 8 (ST9). As a result, as illustrated in FIG. 29C, the resin 8 coated over the LED element 5 is thermally cured into the resin 8*, and becomes in a fixed state within the LED mounting portion 4b. Then, the substrate 4 after the resin has been cured is transmitted to the singulating device M6 in which the substrate 4 is cut for each of the singulated substrates 4a, to thereby singulate the substrate 4 into the LED packages PKG, as illustrated in FIG. 29D (ST10). As a result, the LED package PKG is completed.

As described above, the LED package manufacturing system 1 according to the above embodiment includes: the component mounting device M1 that mounts the plurality of LED element 5 on the substrate 4; the element characteristic information supply means for supplying the information obtained by measuring the light emission wavelengths of the plurality of LED elements 5, individually, in advance, as the element characteristic information 12; the resin information supplying means for supplying the information that associates the appropriate resin coating amount of the resin 8 for obtaining the LED package PKG providing the specific light emission characteristic with the element characteristic information 12 as the resin coating information 14; the map data creating means for creating the map data 18 that associates the mounting position information 71a indicative of the position of the LED element 5 mounted by the component mounting device M1 on the substrate 4 with the element characteristic information 12 on the above LED element 5, for each substrate 4; and the resin coating device M4 that coats the resin 8 of the appropriate resin coating amount for providing the specified light emission characteristic on the respective LED elements mounted on the substrate 4 on the basis of the map data 18 and the resin coating information 14.

The resin coating device M4 includes: the resin coating unit C that discharges the resin 8 with the variable coating amount to coat the resin 8 at the arbitrary position to be coated; the coating control unit 36 that controls the resin coating unit C, to thereby execute the measurement coating processing for trial-coating the resin 8 on the translucent member 41 for the light emission characteristic measurement, and the production coating processing for coating the resin 8 on the LED element 5 for the actual production; the translucent member placement portion 53 on which the translucent member 41 that includes the light source portion that emits the excitation light for exciting the phosphor, and has been trial-coated with the resin 8 in the measurement coating processing is mounted; the light emission characteristic measurement portion that irradiates the resin 8 coated on the translucent member 41 with the excitation light emitted from the light source portion to measure the light emission characteristic of the light emitted by the resin 8; the coating amount derivation processing unit 38 that obtains the deviation between the measurement result of the light emission characteristic measurement portion and the light emission characteristic specified in advance, and corrects the appropriate resin coating amount on the basis of the deviation, to thereby derive the appropriate resin coating amount for the actual production to be coated on the LED element 5; and the production execution processing unit 37 that instructs the coating control unit 36 about the derived appropriate resin coating amount, to thereby execute the production coating processing for coating the LED element 5 with the resin of the appropriate resin coating amount.

With the above configuration, in the resin coating used in the manufacture of the LED package PKG in which the LED element 5 is coated with the resin containing the phosphor therein, the translucent member 41 that has been trial-coated with the resin 8 for the light emission characteristic measurement is placed on the translucent member placement portion 53, the excitation light that excites the phosphor is emitted from the light source unit 42 arranged above, the resin 8 coated on the translucent member 41 is irradiated with the excitation light from above to obtain the deviation between the measurement result obtained by measuring the light emission characteristic of the light obtained by receiving the light emitted by the resin 8 from below the translucent member 41, and the light emission characteristic specified in advance, and the appropriate resin coating amount of the resin to be coated on the LED element 5 for the actual production can be derived on the basis of the deviation. As a result, even if the light emission wavelength of the individual LED elements 5 is varied, the light emission characteristic of the LED package PKG can be equalized to improve the production yield.

Also, in the resin coating device M4 according to this embodiment, the translucent member 41 is reeled off by the recovery reel 48 while being peeled out of the supply reel 47. With the above configuration, not only a disposal of the used translucent member 41 can be facilitated, but also the forward movement and the backward movement of the translucent member 41 can be smoothed with the rotation of the recovery reel 48 together with the supply reel 47. Also, since the supply reel 47 and the recovery reel 48 are disposed on the same shaft member, the overall resin coating device M4 can be downsized. In the above-mentioned embodiment, the translucent member 41 is formed of the emboss tape having the emboss portion 41a. However, the translucent member 41 is not always formed of the emboss tape (in this case, the attachment of the translucent member 41 onto the recovery reel 48 needs to be conducted by another method without depending on the translucent member fixing ring 48d).

Also, in the LED package manufacturing system 1 configured as described above, the respective devices of the management computer 3 and the component mounting device M1 to the singulating device M6 are configured to be connected by the LAN system 2. However, the LAN system 2 is not always essential. That is, if there is provided storage means for storing the element characteristic information 12 and the resin coating information 14 prepared in advance and transmitted from the external for each LED package PKG, and there is provided data supply means that can supply the element characteristic information 12 to the component mounting device M1, and also supply the resin coating information 14 and the map data 18 to the resin coating device M4, from the storage means any time as occasion demands, those means can realize the function of the LED package manufacturing system 1 according to this embodiment.

The present invention is based on Japanese Patent Application No. 2012-031285 filed on Feb. 16, 2012, and content thereof is incorporated herein by reference.

Industrial Applicability

The LED package manufacturing system according to the present invention has the advantages that even if the light emission wavelength of the individual LED elements is varied, the light emission characteristic of the LED package PKG can be equalized to improve the production yield, and can be used in the field of manufacturing the LED package configured to cover the LED elements with the resin containing the phosphor Also, in the above-mentioned embodiment, the translucent member supply and recovery portions including the supply reel 47 and the recovery reel 48 is attached to the base portion 45 of the resin coating device M4 so as to be integrated with the light emission inspection portion including the light source unit 42, the spectrometer 43, and the integrating sphere 44. However, the translucent member supply and recovery portion including the supply reel 47 and the recovery reel 48 may be configured to be provided independently from the light emission inspection portion.

LIST OF REFERENCE SIGNS

1, LED package manufacturing system
2, LAN system
4, substrate
4a, singulated substrate
4b, LED mounting portion
4c, reflection portion
5, LED element
8, resin
12, element characteristic information
13A, 13B, 13C, 13D, and 13E, LED sheet
14, resin coating information
18, map data
23, resin adhesive
24, adhesive transfer mechanism
25, component supply mechanism 26, component mounting mechanism
32, resin discharge head
33, dispenser
33a, discharge nozzle
40, 140, trial coating/measurement unit
40a, trial coating/stage
41, translucent member
42, light source unit
43, spectrometer
44, integrating sphere
47, supply reel
48, recovery reel
48e, torque limiter
51, sprocket drive motor (drive source)
53, 141, translucent member placement portion
54, irradiation portion
56, support shaft (shaft member)
C, resin coating unit
PKG, LED package

The invention claimed is:

1. A resin coating device that coats a resin over an LED element mounted on a substrate for use in an LED package manufacturing system that manufactures an LED package in which the LED element mounted on the substrate is covered with the resin containing a phosphor therein, the resin coating device comprising:
a resin coating unit that discharges the resin with a variable coating amount to coat the resin at an arbitrary position to be coated;
a coating control unit that executes measurement coating processing for trial-coating a translucent member reeled off by a recovery reel while being reeled out of a supply reel with a resin for measurement of a light emission characteristic while controlling the resin coating unit, and production coating processing for coating the resin on the LED element for actual production;
a light source unit that emits an excitation light that excites the phosphor;
a translucent member placement portion on which the translucent member that has been trial-coated with the resin in the measurement coating processing is placed;
a light emission characteristic measurement unit that measures the light emission characteristic of a light emitted from the resin by irradiating the resin coated on the translucent member with the excitation light emitted from the light source unit;
a coating amount derivation processing unit that derives an appropriate resin coating amount of the resin to be coated on the LED element for the actual production on the basis of a measurement result of the light emission characteristic measurement unit and a light emission characteristic specified in advance; and
a production execution processing unit that instructs the coating control unit about the appropriate resin coating amount to execute the production coating processing for coating the appropriate resin coating amount of resin on the LED element,
wherein the supply reel and the recovery reel are arranged on a same shaft member, and when the translucent member is moved forward by actuation of a drive source for advancing the translucent member, one of the supply reel and the recovery reel is rotated while being pulled by the translucent member to reel out the translucent member, and the other reel is rotationally driven through a torque limiter disposed on the shaft member to reel off the translucent member.

2. The resin coating device according to claim 1, wherein the recovery reel comprises a cylindrical member on which the translucent member is wound and a translucent member fixing ring detachably disposed on an outer surface of the cylindrical member.

3. The resin coating device according to claim 2, wherein a locking projection is disposed on the outer surface of the cylindrical member and a projection locking groove is disposed on an inner surface of the translucent member fixing ring, the locking projection of the cylindrical member is configured to be inserted into the locking groove of the translucent member fixing ring so that the translucent member fixing ring is configured to rotate integrally with the cylindrical member when the cylindrical member rotates about the shaft member.

4. The resin coating device according to claim 3, wherein an emboss portion is provided on the translucent member and the emboss portion fits in a gap provided between the locking projection of the cylindrical member and the locking groove of the translucent member.

5. A resin coating method that coats a resin over an LED element mounted on a substrate for use in an LED package manufacturing system that manufactures an LED package in which the LED element mounted on the substrate is covered with the resin containing a phosphor therein, the resin coating method comprising:
a measurement coating step of trial-coating a translucent member reeled off by a recovery reel while being reeled out of a supply reel with a resin for measurement of a light emission characteristic;
a translucent member placing step of placing the translucent member trial-coated with the resin on a translucent member placement portion;
a light emission characteristic measuring step of measuring the light emission characteristic of a light emitted from the resin by irradiating the resin coated on the translucent member with an excitation light emitted from a light source unit that emits the excitation light for exciting the phosphor;
a coating amount derivation processing step of deriving an appropriate resin coating amount of the resin to be coated on the LED element for the actual production on the basis of a measurement result in the light emission characteristic measurement step, and a light emission characteristic specified in advance; and
a production executing step of instructing a coating control unit that controls the resin discharge unit about the derived appropriate resin coating amount, to execute the production coating processing for coating the appropriate resin coating amount of resin on the LED element,
wherein the supply reel and the recovery reel are arranged on a same shaft member, and when the translucent member is moved forward by actuation of a drive source for advancing the translucent member, one of the supply reel and the recovery reel is rotated while being pulled by the translucent member to reel out the translucent member, and the other reel is rotationally driven through a torque limiter disposed on the shaft member to reel off the translucent member.

* * * * *